US008691514B2

(12) United States Patent
Inokuchi et al.

(10) Patent No.: US 8,691,514 B2
(45) Date of Patent: Apr. 8, 2014

(54) METHOD FOR SELECTIVE CONTROL OF HELPER T CELL FUNCTION

(75) Inventors: Jinichi Inokuchi, Sendai (JP); Masakazu Nagafuku, Sendai (JP); Isao Ohno, Sendai (JP); Kaori Okuyama, Sendai (JP)

(73) Assignee: Japan Science and Technology Agency, Kawaguchi-shi, Saitama (JP)

( * ) Notice: Subject to any disclaimer, the term of this patent is extended or adjusted under 35 U.S.C. 154(b) by 0 days.

(21) Appl. No.: 13/126,140

(22) PCT Filed: Oct. 30, 2009

(86) PCT No.: PCT/JP2009/068671
§ 371 (c)(1),
(2), (4) Date: Jul. 1, 2011

(87) PCT Pub. No.: WO2010/050584
PCT Pub. Date: May 6, 2010

(65) Prior Publication Data
US 2011/0262441 A1   Oct. 27, 2011

(30) Foreign Application Priority Data

Oct. 31, 2008 (JP) ................. 2008-281890

(51) Int. Cl.
*G01N 33/53* (2006.01)
(52) U.S. Cl.
USPC ....................................... 435/7.21; 435/7.24
(58) Field of Classification Search
None
See application file for complete search history.

(56) References Cited

U.S. PATENT DOCUMENTS

| 2007/0224200 A1 | 9/2007 | Elbawab et al. |
| 2007/0270350 A1 | 11/2007 | Singh |

FOREIGN PATENT DOCUMENTS

| EP | 1797898 A1 | 6/2007 |
| JP | 10-298181 | 11/1998 |
| JP | 98/48805 | 11/1998 |
| JP | 99/32122 | 7/1999 |
| JP | 2000-053653 | 2/2000 |
| JP | 2005/005636 | 1/2005 |
| JP | 2007-516294 | 6/2007 |
| JP | 2007-536292 | 12/2007 |
| WO | WO-2005108600 A1 | 11/2005 |

OTHER PUBLICATIONS

English language translation of the International prelminary report on patentability for PCT/JP2009/068671, Dec. 3, 2010, pp. 1-11.*
Puri et al., AIDS 2004, 18:849-858.*
European Search Report mailed Nov. 2, 2012 issued in EP Application No. EP 09823694.6.
Yumiko Azuma, et al., "Recombinant Human Hexamer-Dominant IgM Monoclonal Antibody to Ganglioside GM3 for Treatment of Melanoma," Clinical Cancer Research, May 1, 2007, vol. 13, No. 9, pp. 2745-2750.
Sumitaka Matsuo, et al., "Enhancement of FK-506 Activities by Ganglioside (GM3) in Vivo," Life Sciences, 1995, vol. 57, No. 13, pp. 165-169.
N. K. Golovanova, et al., "Development of Antibody to Human GM3 Synthase and Immunodetection of the Enzyme in Human Tissues," Biochemistry, Mar. 1, 2004, vol. 69, No. 3, pp. 275-280.
J. W. K. Chu, et al., "Gangliosides interact with Interleukin-4 and inhibit interleukin-4-stimulated helper T-cell proliferation," Immunology, 1995, vol. 84, pp. 396-403.
Kai Simons et al., "Lipid Rafts and Signal Transduction," *Nature Reviews—Molecular Cell Biology*, vol. 1, pp. 31-39, Oct. 2000.
Peter W. Janes et al., "The role of lipid rafts in T cell antigen receptor (TCR) signaling," *Seminars in Immunology*, vol. 12, pp. 23-34, 2000.
Miroslava Potapenko et al., "Gangliosides as Immunomodulators," *Adv. Exp. Med. Biol.*, vol. 601, pp. 195-203, 2007.
International Search Report dated Dec. 8, 2009 of PCT/JP2009/068671, filed Oct. 30, 2009.
B. Felding-Habermann et al., "A Ceramide Analogue Inhibits T Cell Proliferative Response through Inhibition of Glycosphingolipid Synthesis and Enhancement of *N,N*-Dimethylsphingosine Synthesis", Biochemistry, 1990, vol. 29, No. 26, pp. 6314-6322.
M. Simpson et al., "Infantile-onset symptomatic epilepsy syndrome caused be a homozygous loss-of-function mutation of GM3 synthase", Nature Genetics, Nov. 2004, vol. 36, No. 11, pp. 1225-1229.

* cited by examiner

*Primary Examiner* — Zachary Skelding
(74) *Attorney, Agent, or Firm* — Drinker Biddle & Reath LLP

(57) ABSTRACT

The present invention relates to selectively controlling the function of a helper T cell. In the present invention, a mouse lacking a gene involved in ganglioside biosynthesis (ganglioside GM3 synthetase gene) (SAT-I KO) was produced and analyzed. As a result, the present invention provides, for example, a method for screening a substance which induces selective suppression of the function of a helper T cell in an immune response, including control of production of a sphingoglycolipid in the helper T cell, and moderation or suppression of an excessive immune response caused by the suppression of the function, that is, a substance having an immunosuppression activity, an anti-asthmatic action and/or an anti-allergic action.

3 Claims, 9 Drawing Sheets

A

B

C

Antigen-specific immune response in T cell subsets of SAT-I KO mouse

Superantigen-specific immune response in T cell subsets of SAT-I KO mouse

SEQUENCE LISTING

```
<160> NUMBER OF SEQ ID NOS: 8

<210> SEQ ID NO 1
<211> LENGTH: 1188
<212> TYPE: DNA
<213> ORGANISM: Homo sapiens
<220> FEATURE:
```

```
<221> NAME/KEY: misc_feature
<222> LOCATION: (1)..(1188)
<223> OTHER INFORMATION: Human SAT-I
<220> FEATURE:
<221> NAME/KEY: CDS
<222> LOCATION: (1)..(1188)

<400> SEQUENCE: 1
```

| | | | | | | | | | | | | | | | | |
|---|---|---|---|---|---|---|---|---|---|---|---|---|---|---|---|---|
| atg | gct | tct | gtt | cca | atg | cca | agt | gag | tac | acc | tat | gtg | aaa | ctg | aga | 48 |
| Met | Ala | Ser | Val | Pro | Met | Pro | Ser | Glu | Tyr | Thr | Tyr | Val | Lys | Leu | Arg | |
| 1 | | | | 5 | | | | | 10 | | | | | 15 | | |
| agt | gat | tgc | tcg | agg | cct | tcc | ctg | caa | tgg | tac | acc | cga | gct | caa | agc | 96 |
| Ser | Asp | Cys | Ser | Arg | Pro | Ser | Leu | Gln | Trp | Tyr | Thr | Arg | Ala | Gln | Ser | |
| | | | 20 | | | | 25 | | | | | 30 | | | | |
| aag | atg | aga | agg | ccc | agc | ttg | tta | tta | aaa | gac | atc | ctc | aaa | tgt | aca | 144 |
| Lys | Met | Arg | Arg | Pro | Ser | Leu | Leu | Leu | Lys | Asp | Ile | Leu | Lys | Cys | Thr | |
| | | 35 | | | | | 40 | | | | | 45 | | | | |
| ttg | ctt | gtg | ttt | gga | gtg | tgg | atc | ctt | tat | atc | ctc | aag | tta | aat | tat | 192 |
| Leu | Leu | Val | Phe | Gly | Val | Trp | Ile | Leu | Tyr | Ile | Leu | Lys | Leu | Asn | Tyr | |
| 50 | | | | | 55 | | | | | 60 | | | | | | |
| act | act | gaa | gaa | tgt | gac | atg | aaa | aaa | atg | cat | tat | gtg | gac | cct | gac | 240 |
| Thr | Thr | Glu | Glu | Cys | Asp | Met | Lys | Lys | Met | His | Tyr | Val | Asp | Pro | Asp | |
| 65 | | | | 70 | | | | | 75 | | | | | 80 | | |
| cat | gta | aag | aga | gct | cag | aaa | tat | gct | cag | caa | gtc | ttg | cag | aag | gaa | 288 |
| His | Val | Lys | Arg | Ala | Gln | Lys | Tyr | Ala | Gln | Gln | Val | Leu | Gln | Lys | Glu | |
| | | | 85 | | | | 90 | | | | | 95 | | | | |
| tgt | cgt | ccc | aag | ttt | gcc | aag | aca | tca | atg | gcg | ctg | tta | ttt | gag | cac | 336 |
| Cys | Arg | Pro | Lys | Phe | Ala | Lys | Thr | Ser | Met | Ala | Leu | Leu | Phe | Glu | His | |
| | | 100 | | | | | 105 | | | | | 110 | | | | |
| agg | tat | agc | gtg | gac | tta | ctc | cct | ttt | gtg | cag | aag | gcc | ccc | aaa | gac | 384 |
| Arg | Tyr | Ser | Val | Asp | Leu | Leu | Pro | Phe | Val | Gln | Lys | Ala | Pro | Lys | Asp | |
| | 115 | | | | | 120 | | | | | 125 | | | | | |
| agt | gaa | gct | gag | tcc | aag | tac | gat | cct | cct | ttt | ggg | ttc | cgg | aag | ttc | 432 |
| Ser | Glu | Ala | Glu | Ser | Lys | Tyr | Asp | Pro | Pro | Phe | Gly | Phe | Arg | Lys | Phe | |
| 130 | | | | | 135 | | | | | 140 | | | | | | |
| tcc | agt | aaa | gtc | cag | acc | ctc | ttg | gaa | ctc | ttg | cca | gag | cac | gac | ctc | 480 |
| Ser | Ser | Lys | Val | Gln | Thr | Leu | Leu | Glu | Leu | Leu | Pro | Glu | His | Asp | Leu | |
| 145 | | | | 150 | | | | | 155 | | | | | 160 | | |
| cct | gaa | cac | ttg | aaa | gcc | aag | acc | tgt | cgg | cgc | tgt | gtg | gtt | att | gga | 528 |
| Pro | Glu | His | Leu | Lys | Ala | Lys | Thr | Cys | Arg | Arg | Cys | Val | Val | Ile | Gly | |
| | | | 165 | | | | | 170 | | | | | 175 | | | |
| agc | gga | gga | ata | ctg | cac | gga | tta | gaa | ctg | ggc | cac | acc | ctg | aac | cag | 576 |
| Ser | Gly | Gly | Ile | Leu | His | Gly | Leu | Glu | Leu | Gly | His | Thr | Leu | Asn | Gln | |
| | | | 180 | | | | 185 | | | | | 190 | | | | |
| ttc | gat | gtt | gtg | ata | agg | tta | aac | agt | gca | cca | gtt | gag | gga | tat | tca | 624 |
| Phe | Asp | Val | Val | Ile | Arg | Leu | Asn | Ser | Ala | Pro | Val | Glu | Gly | Tyr | Ser | |
| | | 195 | | | | | 200 | | | | | 205 | | | | |
| gaa | cat | gtt | gga | aat | aaa | act | act | ata | agg | atg | act | tat | cca | gag | ggc | 672 |
| Glu | His | Val | Gly | Asn | Lys | Thr | Thr | Ile | Arg | Met | Thr | Tyr | Pro | Glu | Gly | |
| | 210 | | | | | 215 | | | | | 220 | | | | | |
| gca | cca | ctg | tct | gac | ctt | gaa | tat | tat | tcc | aat | gac | tta | ttt | gtt | gct | 720 |
| Ala | Pro | Leu | Ser | Asp | Leu | Glu | Tyr | Tyr | Ser | Asn | Asp | Leu | Phe | Val | Ala | |
| 225 | | | | | 230 | | | | | 235 | | | | | 240 | |
| gtt | tta | ttt | aag | agt | gtt | gat | ttc | aac | tgg | ctt | caa | gca | atg | gta | aaa | 768 |
| Val | Leu | Phe | Lys | Ser | Val | Asp | Phe | Asn | Trp | Leu | Gln | Ala | Met | Val | Lys | |
| | | | | 245 | | | | | 250 | | | | | 255 | | |
| aag | gaa | acc | ctg | cca | ttc | tgg | gta | cga | ctc | ttc | ttt | tgg | aag | cag | gtg | 816 |
| Lys | Glu | Thr | Leu | Pro | Phe | Trp | Val | Arg | Leu | Phe | Phe | Trp | Lys | Gln | Val | |
| | | | 260 | | | | | 265 | | | | | 270 | | | |
| gca | gaa | aaa | atc | cca | ctg | cag | cca | aaa | cat | ttc | agg | att | ttg | aat | cca | 864 |
| Ala | Glu | Lys | Ile | Pro | Leu | Gln | Pro | Lys | His | Phe | Arg | Ile | Leu | As

| | | |
|---|---|---|
| gtt atc atc aaa gag act gcc ttt gac atc ctt cag tac tca gag cct<br>Val Ile Ile Lys Glu Thr Ala Phe Asp Ile Leu Gln Tyr Ser Glu Pro<br>290                                  295                                  300 | 912 |
| cag tca agg ttc tgg ggc cga gat aag aac gtc ccc aca atc ggt gtc<br>Gln Ser Arg Phe Trp Gly Arg Asp Lys Asn Val Pro Thr Ile Gly Val<br>305                        310                        315                        320 | 960 |
| att gcc gtt gtc tta gcc aca cat ctg tgc gat gaa gtc agt ttg gcg<br>Ile Ala Val Val Leu Ala Thr His Leu Cys Asp Glu Val Ser Leu Ala<br>                        325                        330                        335 | 1008 |
| ggt ttt gga tat gac ctc aat caa ccc aga aca cct ttg cac tac ttc<br>Gly Phe Gly Tyr Asp Leu Asn Gln Pro Arg Thr Pro Leu His Tyr Phe<br>                340                        345                        350 | 1056 |
| gac agt caa tgc atg gct gct atg aac ttt cag acc atg cat aat gtg<br>Asp Ser Gln Cys Met Ala Ala Met Asn Phe Gln Thr Met His Asn Val<br>                        355                        360                        365 | 1104 |
| aca acg gaa acc aag ttc ctc tta aag ctg gtc aaa gag gga gtg gtg<br>Thr Thr Glu Thr Lys Phe Leu Leu Lys Leu Val Lys Glu Gly Val Val<br>370                                  375                                  380 | 1152 |
| aaa gat ctc agt gga ggc att gat cgt gaa ttt tga<br>Lys Asp Leu Ser Gly Gly Ile Asp Arg Glu Phe<br>385                                  390                        395 | 1188 |

```
<210> SEQ ID NO 2
<211> LENGTH: 395
<212> TYPE: PRT
<213> ORGANISM: Homo sapiens

<400> SEQUENCE: 2
```

Met Ala Ser Val Pro Met Pro Ser Glu Tyr Thr Tyr Val Lys Leu Arg
1               5                   10                  15

Ser Asp Cys Ser Arg Pro Ser Leu Gln Trp Tyr Thr Arg Ala Gln Ser
            20                  25                  30

Lys Met Arg Arg Pro Ser Leu Leu Leu Lys Asp Ile Leu Lys Cys Thr
        35                  40                  45

Leu Leu Val Phe Gly Val Trp Ile Leu Tyr Ile Leu Lys Leu Asn Tyr
    50                  55                  60

Thr Thr Glu Glu Cys Asp Met Lys Lys Met His Tyr Val Asp Pro Asp
65                  70                  75                  80

His Val Lys Arg Ala Gln Lys Tyr Ala Gln Gln Val Leu Gln Lys Glu
                85                  90                  95

Cys Arg Pro Lys Phe Ala Lys Thr Ser Met Ala Leu Leu Phe Glu His
            100                 105                 110

Arg Tyr Ser Val Asp Leu Leu Pro Phe Val Gln Lys Ala Pro Lys Asp
        115                 120                 125

Ser Glu Ala Glu Ser Lys Tyr Asp Pro Pro Phe Gly Phe Arg Lys Phe
    130                 135                 140

Ser Ser Lys Val Gln Thr Leu Leu Glu Leu Leu Pro Glu His Asp Leu
145                 150                 155                 160

Pro Glu His Leu Lys Ala Lys Thr Cys Arg Arg Cys Val Val Ile Gly
                165                 170                 175

Ser Gly Gly Ile Leu His Gly Leu Glu Leu Gly His Thr Leu Asn Gln
            180                 185                 190

Phe Asp Val Val Ile Arg Leu Asn Ser Ala Pro Val Glu Gly Tyr Ser
        195                 200                 205

Glu His Val Gly Asn Lys Thr Thr Ile Arg Met Thr Tyr Pro Glu Gly
    210                 215                 220

Ala Pro Leu Ser Asp Leu Glu Tyr Tyr Ser Asn Asp Leu Phe Val Ala

```
                    225                 230                 235                 240
Val Leu Phe Lys Ser Val Asp Phe Asn Trp Leu Gln Ala Met Val Lys
                        245                 250                 255

Lys Glu Thr Leu Pro Phe Trp Val Arg Leu Phe Phe Trp Lys Gln Val
            260                 265                 270

Ala Glu Lys Ile Pro Leu Gln Pro Lys His Phe Arg Ile Leu Asn Pro
        275                 280                 285

Val Ile Ile Lys Glu Thr Ala Phe Asp Ile Leu Gln Tyr Ser Glu Pro
    290                 295                 300

Gln Ser Arg Phe Trp Gly Arg Asp Lys Asn Val Pro Thr Ile Gly Val
305                 310                 315                 320

Ile Ala Val Val Leu Ala Thr His Leu Cys Asp Glu Val Ser Leu Ala
                    325                 330                 335

Gly Phe Gly Tyr Asp Leu Asn Gln Pro Arg Thr Pro Leu His Tyr Phe
                340                 345                 350

Asp Ser Gln Cys Met Ala Ala Met Asn Phe Gln Thr Met His Asn Val
            355                 360                 365

Thr Thr Glu Thr Lys Phe Leu Leu Lys Leu Val Lys Glu Gly Val Val
        370                 375                 380

Lys Asp Leu Ser Gly Gly Ile Asp Arg Glu Phe
385                 390                 395

<210> SEQ ID NO 3
<211> LENGTH: 1245
<212> TYPE: DNA
<213> ORGANISM: Mus musculus
<220> FEATURE:
<221> NAME/KEY: misc_feature
<222> LOCATION: (1)..(1245)
<223> OTHER INFORMATION: Mouse SAT-I
<220> FEATURE:
<221> NAME/KEY: CDS
<222> LOCATION: (1)..(1245)

<400> SEQUENCE: 3 atg cac aca gag gcg gtg ggc ggc gcg gcg cgg agg ccc cag aag ctg      48
Met His Thr Glu Ala Val Gly Gly Ala Ala Arg Arg Pro Gln Lys Leu
1               5                   10                  15 cga agc caa gca gcg gca cct gcc tgc cga gca atg cca agt gag ttc      96
Arg Ser Gln Ala Ala Ala Pro Ala Cys Arg Ala Met Pro Ser Glu Phe
                20                  25                  30 acc tct gca aag ctg aga agt gat tgc tca agg acc tcc ctg caa tgg     144
Thr Ser Ala Lys Leu Arg Ser Asp Cys Ser Arg Thr Ser Leu Gln Trp
            35                  40                  45 tac acc cga acc cag cac aag atg aga aga ccc agc ttg tta ata aaa     192
Tyr Thr Arg Thr Gln His Lys Met Arg Arg Pro Ser Leu Leu Ile Lys
        50                  55                  60 gac atc tgc aag tgc acg ttg gtt gca ttt gga gtc tgg ctc ctg tac     240
Asp Ile Cys Lys Cys Thr Leu Val Ala Phe Gly Val Trp Leu Leu Tyr
65                  70                  75                  80 atc ctc att ttg aat tac acc gct gaa gaa tgt gac atg aaa aga atg     288
Ile Leu Ile Leu Asn Tyr Thr Ala Glu Glu Cys Asp Met Lys Arg Met
                85                  90                  95 cac tat gtg gac cct gac cgg ata aag aga gct cag agc tat gct cag     336
His Tyr Val Asp Pro Asp Arg Ile Lys Arg Ala Gln Ser Tyr Ala Gln
                100                 105                 110 gaa gtc ttg cag aag gaa tgt cgg ccc agg tac gcg aag acg gct atg     384
Glu Val Leu Gln Lys Glu Cys Arg Pro Arg Tyr Ala Lys Thr Ala Met
            115                 120                 125 gct ctg tta ttt gag gac agg tac agc atc aac ttg gag cct ttt gtg     432
```

```
Ala Leu Leu Phe Glu Asp Arg Tyr Ser Ile Asn Leu Glu Pro Phe Val
    130                 135                 140 cag aag gtc ccc acg gcc agt gaa gct gag ctc aag tat gac ccg cct    480
Gln Lys Val Pro Thr Ala Ser Glu Ala Glu Leu Lys Tyr Asp Pro Pro
145                 150                 155                 160 ttt gga ttc cgg aag ttc tcc agt aaa gtc cag agc ctc ttg gat atg    528
Phe Gly Phe Arg Lys Phe Ser Ser Lys Val Gln Ser Leu Leu Asp Met
                165                 170                 175 ctg ccc gaa cat gac ttt cct gaa cac ttg aga gcc aag gcc tgc aag    576
Leu Pro Glu His Asp Phe Pro Glu His Leu Arg Ala Lys Ala Cys Lys
            180                 185                 190 cgc tgt gtg gtt gtt ggg aac ggg ggc atc ctg cac gga cta gag ctg    624
Arg Cys Val Val Val Gly Asn Gly Gly Ile Leu His Gly Leu Glu Leu
        195                 200                 205 ggt cac gcc ctc aac cag ttc gat gtg gta ata agg ttg aac agt gcg    672
Gly His Ala Leu Asn Gln Phe Asp Val Val Ile Arg Leu Asn Ser Ala
    210                 215                 220 cca gtt gag ggt tac tct gaa cac gtt ggg aat aaa act act ata agg    720
Pro Val Glu Gly Tyr Ser Glu His Val Gly Asn Lys Thr Thr Ile Arg
225                 230                 235                 240 atg act tac cca gag ggt gcg cca ctg tcg gac gtt gaa tac tac gcc    768
Met Thr Tyr Pro Glu Gly Ala Pro Leu Ser Asp Val Glu Tyr Tyr Ala
                245                 250                 255 aat gat ttg ttc gtt act gtt tta ttt aag agt gtt gat ttc aag tgg    816
Asn Asp Leu Phe Val Thr Val Leu Phe Lys Ser Val Asp Phe Lys Trp
            260                 265                 270 ctt caa gca atg gta aaa aat gaa agc ctg ccc ttt tgg gtt cgc ctc    864
Leu Gln Ala Met Val Lys Asn Glu Ser Leu Pro Phe Trp Val Arg Leu
        275                 280                 285 ttc ttt tgg aag caa gtg gca gaa aaa gtc cca ctc cag cca aag cac    912
Phe Phe Trp Lys Gln Val Ala Glu Lys Val Pro Leu Gln Pro Lys His
    290                 295                 300 ttc agg att ttg aac cca gtt atc atc aaa gaa act gcc ttc gac atc    960
Phe Arg Ile Leu Asn Pro Val Ile Ile Lys Glu Thr Ala Phe Asp Ile
305                 310                 315                 320 ctt cag tac tca gag cct cag tca aga ttc tgg ggc cat gat aag aac    1008
Leu Gln Tyr Ser Glu Pro Gln Ser Arg Phe Trp Gly His Asp Lys Asn
                325                 330                 335 atc ccc acg atc ggc gtc att gcc gtt gtc ttg gct aca cat ctg tgt    1056
Ile Pro Thr Ile Gly Val Ile Ala Val Val Leu Ala Thr His Leu Cys
            340                 345                 350 gat gaa gtc agc ctg gca ggc ttt ggc tac gac ctc agt caa ccc agg    1104
Asp Glu Val Ser Leu Ala Gly Phe Gly Tyr Asp Leu Ser Gln Pro Arg
        355                 360                 365 acc cct ctg cac tac ttt gac agt cag tgc atg ggc gcc atg cac tgg    1152
Thr Pro Leu His Tyr Phe Asp Ser Gln Cys Met Gly Ala Met His Trp
    370                 375                 380 cag gtc atg cac aat gtg acc aca gag acc aag ttc ctc ctg aag ctc    1200
Gln Val Met His Asn Val Thr Thr Glu Thr Lys Phe Leu Leu Lys Leu
385                 390                 395                 400 ctc aag gag ggc gtg gtg gag gac ctc agc ggc ggc atc cac tga        1245
Leu Lys Glu Gly Val Val Glu Asp Leu Ser Gly Gly Ile His
                405                 410

<210> SEQ ID NO 4
<211> LENGTH: 414
<212> TYPE: PRT
<213> ORGANISM: Mus musculus

<400> SEQUENCE: 4

Met His Thr Glu Ala Val Gly Gly Ala Ala Arg Arg Pro Gln Lys Leu
```

```
           1               5                  10                  15
Arg Ser Gln Ala Ala Pro Ala Cys Arg Ala Met Pro Ser Glu Phe
                20                  25                  30

Thr Ser Ala Lys Leu Arg Ser Asp Cys Ser Arg Thr Ser Leu Gln Trp
                35                  40                  45

Tyr Thr Arg Thr Gln His Lys Met Arg Arg Pro Ser Leu Leu Ile Lys
            50                  55                  60

Asp Ile Cys Lys Cys Thr Leu Val Ala Phe Gly Val Trp Leu Leu Tyr
65                      70                  75                  80

Ile Leu Ile Leu Asn Tyr Thr Ala Glu Glu Cys Asp Met Lys Arg Met
                85                  90                  95

His Tyr Val Asp Pro Asp Arg Ile Lys Arg Ala Gln Ser Tyr Ala Gln
                100                 105                 110

Glu Val Leu Gln Lys Glu Cys Arg Pro Arg Tyr Ala Lys Thr Ala Met
                115                 120                 125

Ala Leu Leu Phe Glu Asp Arg Tyr Ser Ile Asn Leu Glu Pro Phe Val
                130                 135                 140

Gln Lys Val Pro Thr Ala Ser Glu Ala Glu Leu Lys Tyr Asp Pro Pro
145                 150                 155                 160

Phe Gly Phe Arg Lys Phe Ser Ser Lys Val Gln Ser Leu Leu Asp Met
                165                 170                 175

Leu Pro Glu His Asp Phe Pro Glu His Leu Arg Ala Lys Ala Cys Lys
                180                 185                 190

Arg Cys Val Val Val Gly Asn Gly Gly Ile Leu His Gly Leu Glu Leu
                195                 200                 205

Gly His Ala Leu Asn Gln Phe Asp Val Val Ile Arg Leu Asn Ser Ala
                210                 215                 220

Pro Val Glu Gly Tyr Ser Glu His Val Gly Asn Lys Thr Thr Ile Arg
225                 230                 235                 240

Met Thr Tyr Pro Glu Gly Ala Pro Leu Ser Asp Val Glu Tyr Tyr Ala
                245                 250                 255

Asn Asp Leu Phe Val Thr Val Leu Phe Lys Ser Val Asp Phe Lys Trp
                260                 265                 270

Leu Gln Ala Met Val Lys Asn Glu Ser Leu Pro Phe Trp Val Arg Leu
                275                 280                 285

Phe Phe Trp Lys Gln Val Ala Glu Lys Val Pro Leu Gln Pro Lys His
                290                 295                 300

Phe Arg Ile Leu Asn Pro Val Ile Ile Lys Glu Thr Ala Phe Asp Ile
305                 310                 315                 320

Leu Gln Tyr Ser Glu Pro Gln Ser Arg Phe Trp Gly His Asp Lys Asn
                325                 330                 335

Ile Pro Thr Ile Gly Val Ile Ala Val Val Leu Ala Thr His Leu Cys
                340                 345                 350

Asp Glu Val Ser Leu Ala Gly Phe Gly Tyr Asp Leu Ser Gln Pro Arg
                355                 360                 365

Thr Pro Leu His Tyr Phe Asp Ser Gln Cys Met Gly Ala Met His Trp
                370                 375                 380

Gln Val Met His Asn Val Thr Glu Thr Lys Phe Leu Leu Lys Leu
385                 390                 395                 400

Leu Lys Glu Gly Val Val Glu Asp Leu Ser Gly Gly Ile His
                405                 410
```

<210> SEQ ID NO 5
<211> LENGTH: 25

```
<212> TYPE: DNA
<213> ORGANISM: Artificial Sequence
<220> FEATURE:
<223> OTHER INFORMATION: Primer

<400> SEQUENCE: 5
ggaatccatc cctttctca cagag                                           25

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
tgaactcact tggcattgct gg                                             22

<210> SEQ ID NO 7
<211> LENGTH: 25
<212> TYPE: DNA
<213> ORGANISM: Artificial Sequence
<220> FEATURE:
<223> OTHER INFORMATION: Primer

<400> SEQUENCE: 7
ggaatccatc cctttctca cagag                                           25

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
tgaactcact tggcattgct gg                                             22
```

METHOD FOR SELECTIVE CONTROL OF HELPER T CELL FUNCTION

CROSS REFERENCE TO RELATED APPLICATIONS

This application is the National Stage of International Application No. PCT/JP2009/068671, filed Oct. 30, 2009, and claims benefit of Japanese Application No. 2008-281890, filed Oct. 31, 2008, of which is herein incorporated by reference in its entirety.

REFERENCE TO A SEQUENCE LISTING

A Sequence Listing containing SEQ ID NOS. 1-8 is incorporated herein by reference.

TECHNICAL FIELD

The present invention relates to a pharmaceutical composition having an immunosuppression activity, an anti-asthmatic activity and/or an anti-allergic activity, comprising a selective suppressor for a helper T cell activity. Further, the present invention relates to, for example, a method for screening a substance having an immunosuppression activity, an anti-asthmatic action and/or an anti-allergic action, comprising assaying the ability of a selective suppression for a helper T cell activity.

BACKGROUND ART

T cells are immune cells comprising up 70 to 80% of peripheral blood lymphocytes, and are widely distributed in the spleen and lymph nodes throughout the body to contribute to biological defense. T cells are such cells expressing a T cell antigen receptor (T cell receptor; TCR) on the surface thereof, and play the center role in acquired immune system. Activation of T cells is caused when a TCR on the T cell membrane recognizes a major histocompatibility complex (MHC)+an antigen presented by an antigen-presenting cell. One T cell expresses only one type of antigen-specific TCR, thereby exerting an immune response specific to every antigen. Further, T cells express a CD4 or CD8 molecule on the surface thereof, and therefore are classified into the CD4-positive T cell subset and the CD8-positive T cell subset, which form totally different cell populations with different immune functions. The CD4-positive T cell subset is called "helper T cell", and has functions to induce to express the functions of other T cells and to cause differentiation of a B cell into an antibody-producing cell. Meanwhile, the CD8-positive T cell subset is called "killer T cell", and has the function to destroy virus-infected cells, cancer cells, etc. and is involved in rejection, which is a problem at the time of organ transplantation. Further, from a functional standpoint, helper T cells are further classified into 4 subgroups (Th1 cell, Th2 cell, Th17 cell and Treg cell). The Th1 cell is an effector cell differentiated mainly in the presence of IL-12, and mainly produces IFN-γ to induce cellular immunity, which is involved in autoimmune disease and delayed-type allergy. The Th2 cell is an effector cell differentiated mainly in the presence of IL-4, and mainly produces IL-4 to induce humoral immunity, which is involved in immediate-type allergy. The Th17 cell is a recently-identified subgroup. It is believed that the Th17 cell is differentiated in the presence of IL-6 or TGF-β to produce IL-17, which is functionally involved in autoimmune disease. The Treg cell is a CD4-positive T cell that is CD25-positive, which is called "regulatory T cell", and controls immune reaction to contribute to maintenance of homeostasis of the immune system. Thus, T cells play an important role in any pathological condition that involves immunity, such as infection disease, tumor, organ transplantation and allergy. Among others, the CD4-positive helper T cell plays a central role in biological defense, including control of other immune cells. On the other hand, excessive immune response of the helper T cell may cause autoimmune disease and allergy disease. That is, appropriate and moderate activation of the helper T cell is essential for maintenance of homeostasis of the immune system.

As a conventional method for controlling T cell immunity, an immunosuppressive agent is frequently used. However, there is a problem that effects of immunosuppressive agents are non-specific to T cell subsets. As typical immunosuppressive agents, cyclosporine and FK506 are known, but these agents suppress activation of all types of the T cells. Steroid-based agents are also widely used for treating autoimmune disease and allergy disease. However, there is a problem that these agents exert effects which are nonspecific to cells and at once have strong side effects. Thus, a method for selective control of a helper T cell function has not been established yet.

Gangliosides are a group of sphingoglycolipids having sialic acid, and all endogenous sphingoglycolipids are biosynthesized from ceramide through a series of enzyme reactions (FIG. 1). GM3 is a molecule that is the origin of all gangliosides, and is synthesized from lactosylceramide by GM3 biosynthetic enzyme (sialic acid transferase I; SAT-I). Gangliosides are expressed in all mammalian cells and constitute a microdomain on the cell membrane called "raft" together with cholesterol and sphingomyelin. According to recent researches, it has been elucidated that the raft functions as an important place for transmitting information from a receptor into the cell (Non-patent document 1). Also in the T cell, the raft provides a place essential for TCR-mediated intracellular signaling. When the raft structure is destroyed using an agent for removing cholesterol from the cell membrane, TCR-mediated signaling is suppressed and the T cell is no longer activated (Non-patent document 2). The functional role of gangliosides in T cell activation has been tested using a method of adding an inhibitor for a biosynthetic enzyme of sphingoglycolipid or an exogenous ganglioside. As a result, however, no significant influence was observed, or various effects were respectively recognized that is caused by adding different gangliosides (Non-patent document 3). In addition, there was no study in which functions of gangliosides with respect to TCR-mediated activation are analyzed in vivo for every T cell subset.

Non-patent document 1: K Simons and D Toomre. Lipid raft and signal transduction. Nat. Rev. Mol. Cell Biol. 1, 31-39, 2000

Non-patent document 2: P. W. Janes, S. C. Ley, A. I. Magee and P. S. Kabouridis. The role of lipid rafts in T cell receptor signaling. Semin. Immunol. 12, 23-34, 2000

Non-patent document 3: M Potapenko, G. V. Shurin and J de Leon. Gangliosides as immunomodulator. Adv. Exp. Med. Biol. 601, 195-203, 2007

DISCLOSURE OF THE INVENTION

Problems to be Solved by the Invention

Pathological conditions that involve immune reactions, such as infection, tumor, organ transplantation rejection and allergy, may be caused by dysfunction or hyperfunction of helper T cells. When the entire immune system including helper T cells and killer T cells is controlled in such pathological conditions, immunodeficiency disease or immune enhancement condition may be caused. From this viewpoint, a method for selectively controlling a function of a helper T cell is desired.

Means for Solving the Problems

The present inventors diligently made researches in order to solve the above-described problems, and produced a mouse lacking a gene involved in ganglioside biosynthesis (ganglioside GM3 synthetase gene) (SAT-I KO), and using this mouse, analyzed the functional role of ganglioside in activation of a T cell subset at an individual level.

As a result, it was found that, by inhibiting ganglioside GM3 biosynthesis, proliferation due to T cell receptor (TCR) stimulus of a helper T cell can be selectively suppressed while the function of a killer T cell is retained. In addition, it was found that, with this selective suppression of proliferation of a helper T cell, inflammatory infiltration can be reduced in an individual.

Accordingly, the present invention provides, for example, a method for selective suppression of a helper T cell proliferation in an immune response, comprising controlling sphingoglycolipid production of a helper T cell, as well as a method for screening a substance which induces moderation or suppression of an excessive immune response caused by such suppression of proliferation, that is, a substance having an immunosuppression activity, an anti-asthmatic action and/or an anti-allergic action.

Specifically, the present invention relates to, for example, a pharmaceutical composition, a screening method and a treatment method as described below:

(1) A pharmaceutical composition having an immunosuppression activity, an anti-asthmatic activity and/or an anti-allergic activity, comprising a selective suppressor for a helper T cell activity.
(2) The composition according to item (1), wherein the selective suppressor for the helper T cell activity is a substance which specifically suppresses proliferation of the helper T cell.
(3) The composition according to item (2), wherein the selective suppressor for the helper T cell activity is a substance which specifically suppresses production of a sphingoglycolipid in the helper T cell.
(4) The composition according to item (3), wherein the sphingoglycolipid is a ganglioside.
(4a) The composition according to item (3), wherein the ganglioside is GM3.
(5) The composition according to item (4), wherein the selective suppressor for the helper T cell activity comprises an antibody against the GM3 ganglioside.
(6) The composition according to any one of items (1) to (4), wherein the selective suppressor for the helper T cell activity is a GM3 synthetase inhibitor.
(7) The composition according to any one of items (1) to (4), wherein the selective suppressor for the helper T cell activity is an antisense nucleic acid, a ribozyme or an RNA having RNAi effect, which inhibits expression of the GM3 synthetase.
(8) A method for screening a substance having an immunosuppression activity, an anti-asthmatic action and/or an anti-allergic action, comprising assaying the ability of the selective suppression for a helper T cell activity.
(9) A method for screening a substance having an immunosuppressive action, an anti-asthmatic action and/or an antiallergic action, comprising contacting a test substance with a helper T cell, and measuring cell proliferation of the helper T cell.
(10) A method for screening a substance having an immunosuppressive action, an anti-asthmatic action and/or an anti-allergic action, comprising contacting a test substance with a helper T cell, and measuring the production amount of a sphingoglycolipid in the helper T cell.
(11) The method according to item (10), wherein the sphingoglycolipid is a ganglioside.
(11a) The method according to item (11), wherein the ganglioside is GM3.
(12) A method for screening a substance having an immunosuppressive action, an anti-asthmatic action and/or an anti-allergic action, comprising contacting a test substance with a helper T cell, and measuring the expression level of a GM3 synthetase in the helper T cell.
(13) The method according to any one of items (8) to (12), comprising administering a test substance, which is confirmed to have cell proliferation activity for the helper T cell in advance, to a nonhuman animal having immune disease, asthma and/or indicating an allergic reaction.
(14) The method according to item (13), wherein the nonhuman animal is a mouse.
(15) The method according to item (13), further comprising comparing the number of infiltrating cells of eosinophils and/or lymphocytes in an inflammatory site of the nonhuman animal with that of a control.
(16) A method for treating immune disease, asthma and/or allergy, wherein an effective amount of a selective suppressor for a helper T cell activity is administered to a subject to selectively control the immune function of the helper T cell.
(17) The method according to item (16), wherein the selective suppressor for a helper T cell activity suppresses proliferation of the helper T cell.
(17a) The method for screening according to item (16), comprising determining a test substance which reduces at least one of a serum IgE concentration, a serum IL-4 concentration and a serum IL-5 concentration in the nonhuman animal.
(18) The method according to item (16), wherein the selective suppressor for the helper T cell activity suppresses the production amount of a sphingoglycolipid expressed in the helper T cell.
(19) The method according to item (18), wherein the sphingoglycolipid is a ganglioside.
(19a) The composition according to item (18), wherein the ganglioside is GM3.
(20) The method according to item (16), wherein the selective suppressor for the helper T cell activity is a GM3 synthetase inhibitor or a substance which inhibits expression of a GM3 synthetase.
(20a) The composition according to item (20), wherein the selective suppressor for the helper T cell activity is an antisense nucleic acid, dsRNA or ribozyme, which inhibits expression of a GM3 synthetase.
(21) A method for selectively controlling the immune function of a helper T cell comprising controlling production of a sphingoglycolipid in the helper T cell.
(22) A method for screening a selective suppressor for a helper T cell activity, comprising:
 (i) contacting the helper T cell with a glucosylceramide synthetase inhibitor D-PDMP and a ganglioside GM3;
 (ii) contacting the helper T cell with a glucosylceramide synthetase inhibitor D-PDMP, a ganglioside GM3 and a test substance; and (iii) determining a test substance which suppresses proliferation of the helper T cell through comparing cell proliferation in (i) with that in (ii).
(23) The method for screening according to item (22), further comprising:
(v) contacting a killer T cell with the test substance under the condition in which the killer T cell can be proliferated; and
(vi) determining a test substance which does not affect cell proliferation of the killer T cell.
(24) A method for screening a selective suppressor for a helper T cell activity, comprising:
(i) contacting the helper T cell with a polynucleotide which inhibits expression of a GM3 synthetase as a test substance; and
(ii) determining a test substance which does not proliferate the helper T cell.
(25) A method for screening a selective suppressor for a helper T cell activity, comprising:
(i) preparing a recombinant mammalian cell in which a reporter gene is expressed downstream of the SAT-I gene promoter;
(ii) contacting the recombinant cell with a test substance under the condition in which the cell is proliferated; and
(iii) determining a test substance which reduces the expression level of the reporter gene.
(26) A method for screening a selective suppressor for a helper T cell activity, comprising:
(i) contacting the helper T cell with a test substance;
(ii) measuring the amount of at least one ganglioside selected from the group consisting of: GM3, GM2, GM1, GD1a and GT1a (a-series); GD3, GD2, GD1b, GT1b and GQ1b (b-series); and GT3, GT2, GT1c, GQ1c and GP1c (c-series) in cell membrane of the cell; and
(iii) selecting a test substance which reduces the amount of the at least one ganglioside.
(27) The method for screening according to any one of items (22) to (26), further comprising determining a test substance where the cell is not proliferated under the coexistence of the test substance and the combination of an anti-CD3 antibody and an anti-CD28 antibody, the coexistence of the test substance and a superantigen, or the coexistence of the test substance and an allogeneic antigen subset, and where the cell is proliferated under the coexistence of the test substance and the combination of Ionomycin and PMA.

Advantageous Effect of the Invention

The pharmaceutical composition of the present invention can specifically control the function of a helper T cell while the function of a killer T cell is retained, and therefore, it is possible to provide a treatment method as a clinically-novel immune control method.

Further, it is believed that the pharmaceutical composition of the present invention or a substance obtained by the screening method of the present invention is useful, for example, for selectively suppressing proliferation of a helper T cell in cell therapy.

BEST MODE FOR CARRYING OUT THE INVENTION

Figure 1:
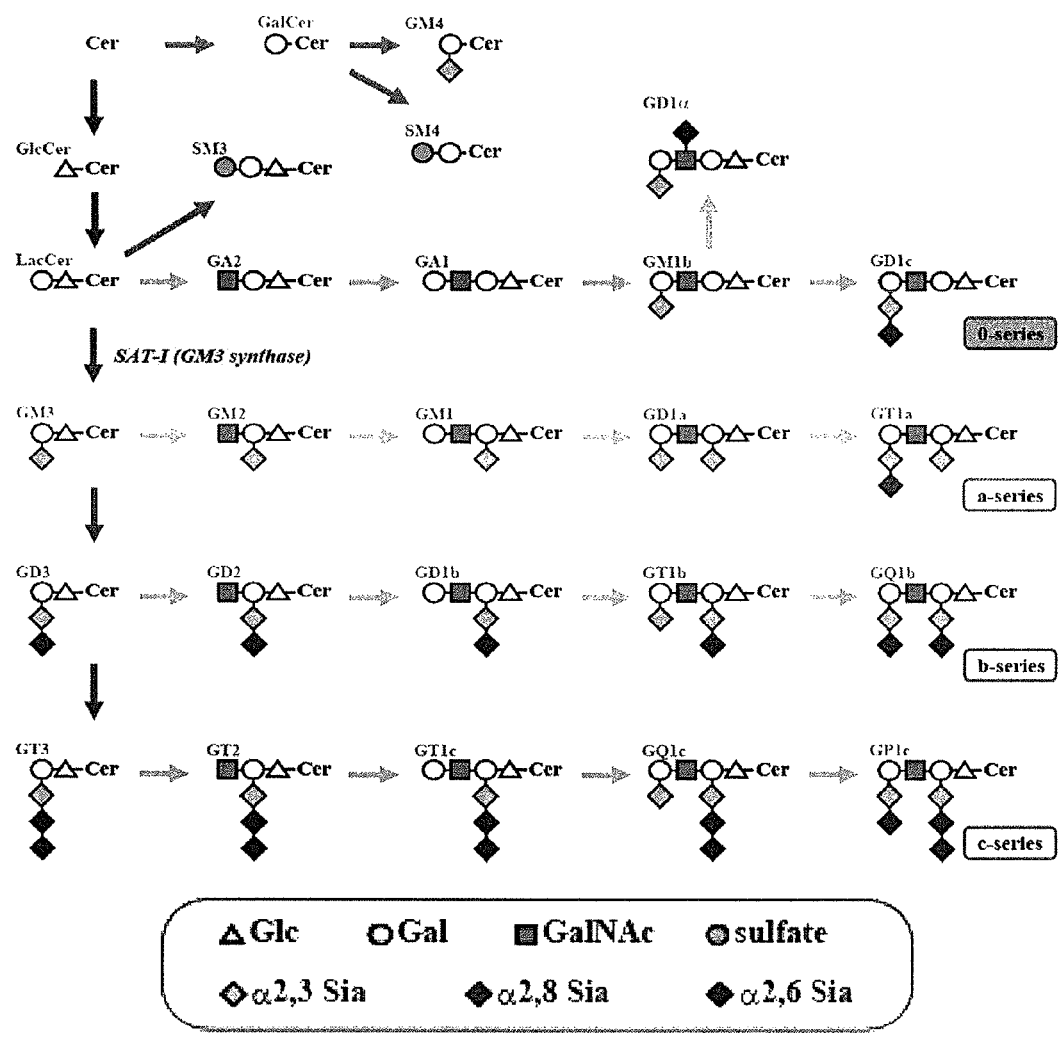
FIG. 1 shows a ganglioside biosynthesis pathway.

1. Pharmaceutical Composition and Treatment Method of the Present Invention

The present invention provides a pharmaceutical composition having an immunosuppression activity, an anti-asthmatic activity and/or an anti-allergic activity, comprising a selective suppressor for a helper T cell activity.

The "selective suppressor for the helper T cell activity" as used herein is a substance which selectively and specifically suppresses the physiologically active functions of the helper T cell (including 4 subgroups, i.e., Th1 cell, Th2 cell, Th17 cell and Treg cell). That is, it is, for example, a substance which acts on the helper T cell while having little effect or no adverse effect on a killer T cell. More specifically, the "selective suppressor for the helper T cell activity" as used herein is a substance whose activity to suppress proliferation of the helper T cell upon stimulation is 10% or higher, preferably 20% or higher, more preferably 40% or higher, even more preferably 60% or higher and still more preferably 80% or higher, as well as whose activity to suppress proliferation of the killer T cell upon stimulation as a control is 20% or lower, more preferably 10% or lower and even more preferably 5% or lower, which is measured according to the method described in "Immunological Protocol" (Hiromitsu Nakauchi Ed., published in September 2004, Yodosha Co., Ltd.).

In addition to cell proliferation, methods for easily indicating the selective activity of a helper T cell include a method in which evaluation is made based on the production amount of IL-4, IL-5 and IFN-γ, which are cytokines selectively produced from the helper T cell upon activation. Moreover, another evaluation can be made based on the expression level of a gene or protein of a transcription factor (T-bet, GATA-3) whose expression is enhanced with activation of the helper T cell.

The "selective suppressor for a helper T cell activity" as preferably used herein is a substance which specifically suppresses proliferation of the helper T cell, and is a substance which specifically suppresses the production amount of a sphingoglycolipid in the helper T cell.

As described above, examples of typical immune responses induced in a living body through the physiologically active functions of the helper T cell include: involvement in autoimmune disease or delayed allergy by producing IFN-γ to induce cellular immunity; involvement in immediate-type allergy by producing IL-4 to induce humoral immunity; functional involvement in autoimmune disease by producing IL-17; and contribution to maintenance of homeostasis of the immune system by controlling immune reaction (Shu L and Paul WE CD4T cells: fates, functions, and faults. Blood, 112, 1557-1569, 2008).

The "immunosuppression activity" in the present invention means an activity to cause suppression, reduction, moderation, remission, improvement, etc. of excessive immune response in the living body (for example, see Gummed J F et al. Newer Immunosuppressive Drugs: A Review. J Am Soc Neprol 10, 1366-1380, 1999). Examples of substances having such an activity include publicly-known immunosuppressive agents such as cyclosporine.

The "anti-asthmatic activity" in the present invention means treating and/or preventing symptoms of asthma. Asthma is a respiratory disease in which inflammation of the airway caused by an allergen, infection by a bacterium or virus, etc. is exacerbated to cause enhancement of airway hypersensitivity or reversible airway narrowing, resulting in symptoms including convulsive wheezing and cough. Examples of currently-used agents for treating asthma include: bronchodilators (β-receptor agonists, xanthine derivatives and anticholinergic agents); adrenocortical hormones (e.g., beclometasone dipropionate as an inhaled steroid agent); and anti-allergic agents (e.g., cromoglycic acid as a histamine release inhibitor, and terfenadine, thromboxane A2 receptor antagonist and leukotriene antagonist as histamine receptor antagonists) (for example, see Asthma Prevention and Management Guideline 2006, edited by Japanese Society of Allergology).

The "anti-allergic activity" in the present invention means treating and/or preventing symptoms of allergy. Immune reaction acts to eliminate foreign substances (antigens) and is a physiological function essential for the living body. Allergy means that this immune reaction excessively acts on a specific antigen. Although it is not clear why allergies are caused, it is believed that there are exogenous causes such as excessive exposure to an antigen and endogenous causes such as inheritance (for example, see Asthma Prevention and Management Guideline 2006, edited by Japanese Society of Allergology).

In the present invention, to "specifically suppress proliferation of the helper T cell" means that only proliferation of the helper T cell of somatic cells is selectively and specifically suppressed. As selective proliferation of the helper T cell, for example, cell proliferation caused by proliferation stimulation mediated by helper T cell-specific CD4 is exemplified. In addition, examples of helper T cell-specific proliferation stimuli include MHC class II molecule-dependent antigens and MHC class II molecule-specific antibodies.

The sphingoglycolipid is a lipid containing sugar, fatty acid and sphingosine as a long-chain base in its molecule. Ganglioside is the general term for the family of sphingoglycolipids containing sialic acid, and is a molecule in which a sugar chain containing sialic acid is covalently bound to a lipid called ceramide. Today, gangliosides with various sugar chain structures are known, and GM3 is the first ganglioside molecule in the biosynthesis pathway (see FIG. 1). That is, all endogenous ganglio-type gangliosides are biosynthesized by a series of enzyme reactions in which ceramide is used as a starting material and a GM3 synthetase firstly works. In the series of enzyme reactions, GM3 is a molecule that is the origin of all gangliosides, and is synthesized from lactosylceramide by GM3 biosynthetic enzyme (SAT-I). The sugar chain portion is sequentially synthesized by glycosyltransferase in the lumen of the Golgi body in the cell using a sugar nucleotide as a donor.

Regarding a specific biosynthesis pathway of ganglio-type gangliosides, as shown in FIG. 1, GM3 is produced from Gal-Glc-Cer by GM3 biosynthetic enzyme (SAT-I), and from this GM3, gangliosides of a-series (GM3, GM2, GM1, GD1a and GT1a), b-series (GD3, GD2, GD1b, GT1b and GQ1b) and c-series (GT3, GT2, GT1c, GQ1c and GP1c) are produced. It is understood in view of the figure that production of these ganglioside molecules is dependent on a GM3 synthetase.

In the present invention, the selective suppressor for a helper T cell activity may specifically inhibit the function of GM3 using an antibody against GM3. Examples of such antibodies include publicly-known monoclonal antibodies having specificity to GM3 (Kotani, M., et al.,: Biochem. Biophys. Acta, 1117, 97-103 (1992)). In a specific embodiment, such antibodies can inhibit the action of GM3 in the cell membrane of the helper T cell. In the context of the present invention, it is understood that the antibody includes a monoclonal antibody, a polyclonal antibody, an anti-idiotype antibody and an antibody fragment (e.g., Fab, and F(ab')2, a Fv variable region, or complementarity determining regions). It is understood that, when the antibody is bound with Ka of $10^{-7}$M or more, preferably $10^{-8}$M or more, the antibody is specific to a GM3 or a GM3 synthetase. The affinity of the monoclonal antibody can be easily determined by those skilled in the art (see Scatchard, Ann. N.Y. Acad. Sci. 51: 660-672, 1949).

In the present invention, the selective suppressor for a helper T cell activity may be a compound which suppresses biosynthesis of GM3. The GM3 synthetase (SAT-I) used herein means a protein comprising the amino acid sequence of SEQ ID NO: 2 or 4, or the amino acid sequence of SEQ ID NO: 2 or 4 having mutations of deletion, substitution, insertion and/or addition of one to several (1 to 9, 1 to 8, 1 to 7, 1 to 6, 1 to 5, 1 to 4, 1 to 3, 1 to 2, or 1) amino acids therein. Regarding biosynthesis of GM3, as shown in FIG. 1, glucosylceramide synthetase acts on ceramide (Cer) to synthesize glucosylceramide (GlcCer), and then lactosylceramide (LacCer) is produced by lactosylceramide synthetase. The GM3 synthetase recognizes this LacCer as a substrate, and synthesizes GM3. That is, those which can inhibit enzyme reactions using substrate analogs of glucosylceramide synthetase, lactosylceramide synthetase and GM3 synthetase, and those which can bind to these enzymes to reduce the GM3 amount are exemplified. Examples of the GM3 synthetase inhibitor of the present invention include: the glucosylceramide biosynthesis inhibitor D-PDMP and analogs thereof (Inokuchi, J., and Radin, N. Preparation of active isomer of 1-phenyl-2-decanoylamino-3-morpholino-1-propanol. J. Lipid Res. 28, 565-571, 1987; Radin N S., et al. Metabolic effects of inhiboting glucosylceramide synthesis with PDMP and other substances. Adv. Lipid. Res. 26, 183-213, 1993; Lee. L., et al. Improved inhibitors of glucosylceramide synthase., J. Biol. Chem. 274, 14662-14669, 1999; Jimbo M., et al. Development of a New Inhibitor of Glucosylceramide Synthase. J. Biochem. 127, 485-491, 2000); and AMP-DNM, which has a different basic structure (N-(5-adamantane-1-yl-methoxy)-pentyl-1-deoxynojirimycin, Pharmacological Inhibition of Glucosylceramide Synthase Enhances Insulin Sensitivity. Diabetes 56, 1341-1349, 2007).

In the present invention, the selective suppressor for a helper T cell activity may be a substance which suppresses expression of the GM3 synthetase. cDNA of the GM3 synthetase (SAT-I) as used herein is represented by, for example, SEQ ID NO: 1 or 3. Examples of such substances which inhibit the expression of the GM3 synthetase include an antisense nucleic acid, a ribozyme and a dsRNA having RNAi effect.

As used herein, the term "nucleic acid" is interchangeable with "polynucleotide", "gene" or "nucleic acid molecule", and a polymer of nucleotide is intended. As used herein, the term "base sequence" is interchangeable with "nucleic acid sequence" or "nucleotide sequence", and is indicated as a sequence of deoxyribonucleotide (abbreviated as A, G, C and T). Further, "a polynucleotide comprising the base sequence of SEQ ID NO: 1 or a fragment thereof" means a polynucleotide comprising a sequence represented by each deoxynucleotide (A, G, C and/or T) of SEQ ID NO: 1 or a fragment thereof.

The nucleic acid in the present invention may be present in the form of an RNA (e.g., mRNA) or a DNA (e.g., cDNA or genome DNA). DNA may be a double strand or a single strand. A single-strand DNA or an RNA may be a coding strand (also known as "sense strand") or a noncoding strand (also known as "antisense strand").

The "substance which inhibits expression of a GM3 synthetase" in the present specification includes suppression of transcription of the GM3 synthetase gene and suppression of translation into a protein. Moreover, it also includes complete termination of expression of DNA as well as reduction of expression thereof.

One embodiment of the "substance which inhibits expression of a GM3 synthetase" is a nucleic acid encoding an antisense chain complementary to the GM3 synthetase gene. The antisense technology is publicly known as a method for suppressing expression of a specific endogenous gene, and is described in various documents (for example, see Hirashima and Inoue, "Shin Seikagaku Jikken Koza 2, Kakusan IV, Idenshi No Fukusei To Hatsugen (New Biochemistry Experimentation Lectures 2, Nucleic Acids IV, Replication and Expression of Genes)", Japanese Biochemical Society Ed., Tokyo Kagaku Dojin Co., Ltd., pp. 319-347, 1993). The antisense nucleic acid can be prepared, for example, based on information of the sequence of cDNA represented by SEQ ID NO: 1 or 3 according to the hosphorothionate method (Stein, Nucleic Acids Res., 16: 3209-3221, 1988). The prepared nucleic acid can be utilized in the form in which it can be directly applied to a cell according to a publicly-known method, and the nucleic acid can transform a desired cell in the form in which it is incorporated into a vector having a publicly-known expression system and appropriately expressed. The sequence of the antisense nucleic acid is preferably complementary to a transcription product of an endogenous gene possessed by a cell to be transformed, while the sequence does not have to be completely complementary thereto as long as expression of the gene can be effectively inhibited. The transcribed RNA preferably has at least 90% (e.g., at least 95%, at least 96%, at least 97%, at least 98%, or at least 99%) complementarity to a transcription product of a target gene. For effectively inhibiting expression of the target gene using the antisense sequence, the length of the antisense nucleic acid is at least 15 bases, preferably at least 100 bases, and more preferably at least 500 bases. Usually, the length of the antisense nucleic acid to be used is less than 5kb, and preferably less than 2.5 kb.

In the present invention, expression of an endogenous GM3 synthetase gene can also be suppressed by utilizing a DNA encoding a ribozyme. The ribozyme means an RNA molecule having catalyst activity, and cleaves a target transcription product of a DNA to inhibit the function of the gene. Regarding the design of ribozymes, various publicly-known documents can be referred to (for example, see FEBS Lett. 228: 228, 1988; FEBS Lett. 239: 285, 1988; Nucl. Acids. Res. 17: 7059, 1989; Nature 323: 349, 1986; Nucl. Acids. Res. 19: 6751, 1991; Protein Eng 3: 733, 1990; Nucl. Acids Res. 19: 3875, 1991; Nucl. Acids Res. 19: 5125, 1991; Biochem Biophys Res Commun 186: 1271, 1992). Further, the "polynucleotide encoding an RNA which suppresses expression of a DNA through cosuppression effect" means a nucleotide which inhibits the function of a DNA to be targeted by "cosuppression".

Moreover, suppression of expression of an endogenous gene in the present invention can also be achieved by transforming a desired cell with a gene having the dominant negative character of a target gene. The gene having the dominant negative character means a gene having the function to eliminate or reduce the activity of an endogenous wild-type gene inherent in a desired cell by being expressed.

Another embodiment of the nucleic acid to be used for suppressing expression of a GM3 synthetase gene is an RNA which suppresses expression of a DNA by RNAi effect. "RNAi" means a phenomenon in which, when a double-strand RNA having a sequence that is identical or similar to a target gene sequence is introduced into a cell, expression of both an exogenous gene introduced and a target endogenous gene is suppressed. Examples of RNAs used herein include double-strand RNAs having 21 to 25 bases causing RNA interference such as dsRNA (double strand RNA), siRNA (small interfering RNA) and shRNA (short hairpin RNA). Such an RNA can be locally delivered to a desired site by a delivery system of a liposome or the like, and can be locally expressed using a vector in which the above-described double-strand RNA can be produced. Methods of preparing and using such a double-strand RNA (dsRNA, siRNA or shRNA) are publicly known from many documents (for example, see Japanese National-phase PCT Laid-Open Patent Publication No. 2002-516062; US Laid-Open Publication No. 2002/086356A; Nature Genetics, 24(2), 180-183, 2000 February; Genesis, 26(4), 240-244, 2000 April; Nature, 407: 6802, 319-20, 2002 Sep. 21; Genes & Dev., Vol. 16, (8), 948-958, 2002 Apr. 15; Proc. Natl. Acad. Sci. USA., 99(8), 5515-5520, 2002 Apr. 16; Science, 296(5567), 550-553, 2002 Apr. 19; Proc Natl. Acad. Sci. USA, 99:9, 6047-6052, 2002 Apr. 30; Nature Biotechnology, Vol. 20 (5), 497-500, 2002 May; Nature Biotechnology, Vol. 20 (5), 500-505, 2002 May; Nucleic Acids Res., 30:10, e46, 2002 May 15).

In the present invention, the pharmaceutical composition having an immunosuppression activity, an anti-asthmatic activity and/or an anti-allergic activity comprises a substance having the action to specifically suppress a helper T cell activity, and can be used for treating or preventing, for example, autoimmune disease, asthma, allergy, infectious disease, tumor, and rejection caused by transplantation of organs, etc. (e.g. renal transplantation, cardiac transplantation and bone-marrow transplantation). The pharmaceutical composition having the action to specifically suppress a helper T cell activity of the present invention is preferably used for treating or preventing rejection caused by transplantation of organs, etc., autoimmune disease, asthma, infectious disease, allergy and tumor, and is more preferably used for treating or preventing autoimmune disease, asthma, infectious disease, allergy, etc. Particularly preferably, the composition is used for treating or preventing asthma and/or allergy disease.

When using the pharmaceutical composition of the present invention, it can be administered, for example, orally, intravenously, through the oral mucosa, rectally, vaginally, transdermally, intranasally, by inhalation, etc., and it is preferably administered orally. The active component of the pharmaceutical composition of the present invention may be blended solely or in combination, and it is also possible to blend a pharmaceutically acceptable carrier or formulation additive therein to provide a formulation. In this case, the active component of the present invention can be contained in the formulation, for example, in an amount of 0.1 to 99.9 wt %.

As the pharmaceutically acceptable carrier or additive, for example, an excipient, a disintegrant, a disintegrating aid, a binder, a lubricant, a coating agent, a dye, a diluent, a dissolving agent, a dissolving aid, a tonicity agent, a pH adjuster, a stabilizer, etc. can be used.

Examples of formulations suitable for oral administration include a powdered drug, a tablet, a capsule, a fine grain agent, a granular agent, a liquid drug and a syrup. In the case of oral administration, various excipients such as microcrystalline cellulose, sodium citrate, calcium carbonate, dipotassium phosphate and glycine can be used in combination with: starch, preferably starch of corn, potato or tapioca; various disintegrants such as alginic acid and some of silicates; and a granulating binder such as polyvinyl pyrrolidone, sucrose, gelatin and gum arabic. Further, in many cases, lubricants such as magnesium stearate, sodium lauryl sulfate and talc are very effective for tablet formation. Such solid composition may be used with a gelatin capsule filled therein. In this regard, examples of preferred substances include lactose or milk sugar as well as a high-molecular-weight polyethylene glycol. When an aqueous suspension and/or elixir is desired for oral administration, active components are used in combination with a sweetener or a flavor and a colorant or a dye, and optionally in combination with an emulsifier and/or a suspending agent, and it can be used together with water, ethanol, propylene glycol, glycerin, a diluent containing a combination thereof, etc.

Examples of preparations suitable for parenteral administration include an injectable agent and a suppository. In the case of parenteral administration, a solution in which the active ingredient of the present invention is dissolved in sesame oil or peanut oil, or a solution in which the active component of the present invention is dissolved in an aqueous solution of propylene glycol can be used. An aqueous solution optionally may be buffered suitably (preferably pH 8 or higher), and a liquid diluent is firstly required to become isotonic. Such an aqueous solution is suitable for intravenous injection, and an oily solution is suitable for intraarticular injection, intramuscular injection and subcutaneous injection. Production of all of these solutions under aseptic conditions can be easily accomplished by the standard formulation technology well-known in the art. Moreover, the active ingredient of the present invention can be administered topically on the skin or the like. In this case, it is desirably administered topically in the form of cream, jelly, paste or ointment according to the standard pharmaceutical practice.

The dose of the pharmaceutical composition of the present invention is not particularly limited, and an appropriate dose can be selected depending on various conditions such as the type of disease, age and symptoms of patient, administration route, therapeutic goal, presence or absence of a concurrent agent, etc. The dose of the pharmaceutical composition of the present invention is, for example, 1 to 5,000 mg, and preferably 10 to 1,000 mg per day for an adult (e.g., bodily weight: 60 kg). The composition of such daily dosage may be administered daily in 2 to 4 divided doses.

2. Screening Method of the Present Invention

The present invention further provides a method for screening a selective suppressor for a helper T cell activity, i.e., a substance having an immunosuppression activity, an anti-asthmatic action and/or an anti-allergic action, comprising assaying the ability of selective suppression for a helper T cell activity. Examples of such screening methods include methods which are carried out in vitro and/or in vivo.

Examples of the screening method of the present invention include a method which comprises contacting a test substance with a helper T cell in vitro and measuring selective cell proliferation in the helper T cell. Examples of the test substance include a peptide, a protein, a nonpeptidic compound, a synthetic compound, a fermentation product, a cell extraction liquid, a plant extraction liquid, an animal tissue extraction liquid and plasma. The helper T cell may be isolated from the living body or may be an established cell. Regarding the measurement of proliferation of the helper T cell, examples of direct measurement methods include a method of visually counting using a hemocytometer and a method using a device such as a Coulter counter and a flow cytometer. Examples of indirect measurement methods include a method using a commercially-available reagent/kit such as a XTT assay kit (e.g., a kit manufactured by R & D systems, MN, USA), and the like. Further, a publicly-known method for excluding dead cells (e.g., trypan blue staining) can be optionally used in combination. In such a screening method, for example, the activity to suppress proliferation of the helper T cell upon stimulation is 10% or higher, preferably 20% or higher, more preferably 40% or higher, even more preferably 60% or higher and still more preferably 80% or higher, and the activity to suppress proliferation of the killer T cell under the same condition as a control is 20% or lower, more preferably 10% or lower and even more preferably 5% or lower, which is measured according to the aforementioned method described in "Immunological Protocol" (Hiromitsu Nakauchi Ed., Yodosha Co., Ltd.).

Examples of the screening method of the present invention include a method comprising contacting a test substance with the helper T cell in vitro and measuring the amount of the selective production of a sphingoglycolipid in the helper T cell. The sphingoglycolipid to be measured is preferably a ganglioside, and more preferably GM3. For purification and quantitative detection of glycolipids, publicly-known methods can be used. For example, the method of Macher B A and Klock J C (J. Biol. Chem. 255, 2092-2096, 1980) or the method of Ledeen et al. (J. Neurochem. 21, 829-839, 1973) can be referred to. Further, for example, it is also possible to employ quantitative detection using an antibody which specifically acts on a ganglioside such as GM3. In such a screening method, for example, the suppression of GM3 production in the helper T cell upon stimulation is 10% or higher, preferably 20% or higher, more preferably 40% or higher, even more preferably 60% or higher and still more preferably 80% or higher, which is measured according to the aforementioned method described in "Immunological Protocol" (Hiromitsu Nakauchi Ed., Yodosha Co., Ltd.).

Examples of the screening method of the present invention include an assay method comprising contacting a test substance with the helper T cell in vitro and assaying a ganglioside composition in the helper T cell. Specifically, it is a method for selecting a test substance which significantly reduces the amount of at least one ganglioside selected from the group consisting of: GM3, GM2, GM1, GD1a and GT1a (a-series); GD3, GD2, GD1b, GT1b and GQ1b (b-series); and GT3, GT2, GT1c, GQ1c and GP1c (c-series). As used herein, "significantly reduce" refers to reduction level by at least 10% or higher, preferably 20% or higher, more preferably 40% or higher, even more preferably 60% or higher, still more preferably 80% or higher, and 90% or higher, as compared to a control.

Examples of the screening method of the present invention include a method comprising contacting a test substance with the helper T cell in vivo and measuring the level of the selective expression of the GM3 synthetase in the helper T cell. As a method for measuring the expression level of the GM3 synthetase, a method mediated by hybridization utilizing a sequence of a GM3 synthetase is exemplified. Examples thereof include Northern Blotting, a method utilizing a probe immobilized on a carrier, a method using a gene chip, and quantitative PCR. In such a screening method, for example, the suppression of the expression of the GM3 synthetase in the helper T cell upon stimulation is 10% or higher, preferably 20% or higher, more preferably 40% or higher, even more preferably 60% or higher, still more preferably 80% or higher, and 90% or higher, which is measured according to the aforementioned method described in "Immunological Protocol" (Hiromitsu Nakauchi Ed., Yodosha Co., Ltd.).

Examples of the test substance in the screening method of the present invention include a polynucleotide which specifically inhibits the expression of the GM3 synthetase. Examples of the form of such a polynucleotide which inhibits the expression of the GM3 synthetase include the aforementioned antisense nucleic acid, ribozyme, double-strand RNA, etc. These polynucleotides which inhibit the expression of the GM3 synthetase can be prepared by a publicly-known method. Moreover, these nucleic acids may be subjected to various chemical modifications.

Examples of the screening method of the present invention also include a method comprising: using a transgenic animal-derived cell or a recombinant cell, in which a reporter gene is connected to the downstream of a promoter of a GM3 synthetase; contacting a test substance with the cell in vivo; and measuring the expression level of the reporter gene in the cell. As a recombinant cell to be used in this method, various cells can be used, and a T cell is preferred, and a helper T cell is more preferred. The gene sequence of the 5'-upstream of the GM3 synthetase gene is described in Kim J-W., et al., Gene 273, 163-171, 2001, and the promoter thereof is described in Kim S-W., et al., Biochim. Biophys. Acta 1578, 84-89, 2002.; and Choi H-J., et al., Biochem. Biophys. Res. Commun. 313, 142-147, 2004. Specifically, putative binding sites of transcription factors AP4, MZF1, SP1, ATF/CREB, NFY, IK2 and LYF1 have been found, and CREB has been additionally found which functions as a PMA-inducible promoter. Preferred examples of proteins encoded by a reporter gene to be used include various publicly-known proteins such as firefly luciferase, Renilla luciferase, green fluorescent protein (GFP), β-galactosidase and alkaline phosphatase. These reporter proteins can be detected using a publicly-known detection method or kit. In such a screening method, for example, the suppression of expression of a reporter protein upon stimulation by a test substance is 10% or higher, preferably 20% or higher, more preferably 40% or higher, 60% or higher, even more preferably 80% or higher, and 90% or higher.

The helper T cell selective ability of a test substance selected in the screening method of the present invention can be confirmed based on cell proliferation of the helper T cell in the presence of various publicly-known T cell receptor stimuli such as the combination of an anti-CD3 antibody and an anti-CD28 antibody, a superantigen and an alloantigen (allogeneic antigen). As a stimulus which is not mediated by a T cell receptor as a control, the combination of Ionomycin and PMA is exemplified, and under this stimulus, both a helper T cell and a killer T cell can be proliferated. See, for example, "Immunological Protocol" (Hiromitsu Nakauchi Ed., Yodosha Co., Ltd.).

The screening method of the present invention may further comprise administering a test substance, which is confirmed to have cell proliferation activity for a helper T cell in advance, to a non-human animal having immune disease, asthma and/or indicating an allergic reaction. In this case, the test substance can add a publicly-known modification, such as modification to allow a specific action on a helper T cell in the living body or utilization of a delivery system specific to the helper T cell.

Alternatively, in the screening method of the present invention, detection may be carried out, for example, based on the amount of a cytokine produced by a helper T cell. Examples of cytokines produced by helper T cells include: IL-2, IL-4, IL-5, IL-6 and IFN-γ, which activate B cells; IL-4, IL-12, IFN-γ and TNF-β, which activate macrophages; IL-3, IL-5 and GM-CSF, which activate eosinophils; and IL-3, IL-4, IL-9, IL-10 and IFN-γ, which activate mast cells. Examples of methods for detecting these cytokines include, but are not limited to, methods of measuring proliferation of cells which are dependent on these cytokines, methods of confirming physiological activities such as antibody production, and methods using antibodies against these cytokines. In such a screening method, for example, the reduction of the production of a specific cytokine by a helper T cell upon stimulation is 10% or higher, preferably 20% or higher, more preferably 40% or higher, even more preferably 60% or higher, still more preferably 80% or higher, and 90% or higher, and the suppression of the production of the specific cytokine by a killer cell under the same condition as a control is 20% or lower, more preferably 10% or lower and even more preferably 5% or lower, as measured according to the aforementioned method described in "Immunological Protocol" (Hiromitsu Nakauchi Ed., Yodosha Co., Ltd.).

Examples of the above-described non-human animal include animals which are generally utilized in tests of pharmaceutical products, such as monkey, chimpanzee, dog, cat, guinea pig, rat, mouse, pig, sheep and horse. The non-human animal is preferably a monkey, chimpanzee, rat or mouse, and more preferably a mouse or rat.

The screening method of the present invention may further comprise, for example, measuring the number of the infiltrating cells such as macrophages, eosinophils, neutrophils, lymphocytes and mast cells in an inflammatory site or the like in vivo. That is, for example, when administering a test substance to a subject having an inflammatory site, if all or at least one of the macrophage, eosinophil, neutrophil, lymphocyte, mast cell and the like in the inflammatory site are significantly reduced, it can be inferred that the test substance is of therapeutic benefit. As used herein, "significantly reduced" refers to reduction by at least 10% or higher, preferably 20% or higher, more preferably 40% or higher, even more preferably 60% or higher, still more preferably 80% or higher, 90% or higher, and 95% or higher, when compared to a control.

The screening method of the present invention may further comprise, for example, measuring the serum IgE concentration in allergic reaction in vivo. For example, when administering a test substance to a subject having an inflammatory site, if the IgE concentration in the blood of the subject is significantly reduced, it can be inferred that the test substance is of therapeutic benefit.

The present invention further provides a method for treating immune disease, asthma and/or allergy, which comprises administering an effective amount of a selective suppressor for a helper T cell activity to a subject, and selectively controlling the immune function of the helper T cell. Further, examples of the selective suppressor for the helper T cell activity include the above-described pharmaceutical composition and a test substance confirmed by the screening method.

In the treatment method of the present invention, as described above, examples of the selective suppressor for the helper T cell activity include: a substance which selectively suppresses proliferation of a helper T cell; a substance which suppresses the production amount of a sphingoglycolipid expressed in a helper T cell; a substance which suppresses the production amount of a ganglioside expressed in a helper T cell; a substance which suppresses the production amount of GM3 expressed in a helper T cell; a GM3 synthetase inhibitor; and a substance which inhibits the expression of the GM3 synthetase. When administering the pharmaceutical composition or the like, the dose thereof can be suitably adjusted in individual cases depending on symptoms, age and gender of a subject to be administered, etc. The dose, the number of dosages, etc. can be suitably adjusted based on medical physician's consideration of age, history, currently-used agents, etc. of a subject.

EXAMPLES

Hereinafter, the present invention will be more specifically described by way of illustrative examples, but the present invention is not limited to these examples.

1. Outline

In order to analyze the role of gangliosides in the immune function in vivo, asthma/allergic reaction of a GM3 synthetase gene-deficient mouse (SAT-I KO mouse) was examined using a model of asthma/allergic reaction against ovalbumin (OVA). As a result, it was demonstrated that GM3 and related gangliosides are involved in induction of allergic immune response and airway inflammation, and it was strongly suggested that gangliosides are essential for the function of the helper T cell.

Therefore, in order to demonstrate the role of gangliosides in the immune function of T cell subsets, TCR-dependent activation of the helper T cell and the killer T cell of the SAT-I KO mouse was compared to that of the wild-type mouse (control mouse). In the SAT-I KO mouse, the gangliosides of a-series (GM3, GM2, GM1, GD1a and GT1a), b-series (GD3, GD2, GD1b, GT1b and GQ1b) and c-series (GT3, GT2, GT1c, GQ1c and GP1c) were completely lacked (see FIG. 1). As a result, it became clear that in the SAT-I KO mouse, the function of the helper T cell was specifically suppressed while the function of the killer T cell was normal. Next, it was examined whether or not the function of the T cell is recovered by exogenously supplying lacked gangliosides or reintroducing the SAT-I gene to the T cell of the SAT-I KO mouse.

2. Regarding Preparation of SAT-I KO Mouse

Figure 2:
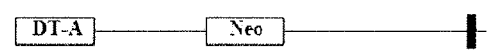
FIG. 2 shows a method for preparing a mouse lacking a GM3 synthetase gene (SAT-I KO).
Figure 2:
Figure 2:
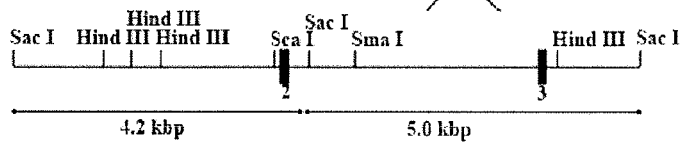
Figure 2:
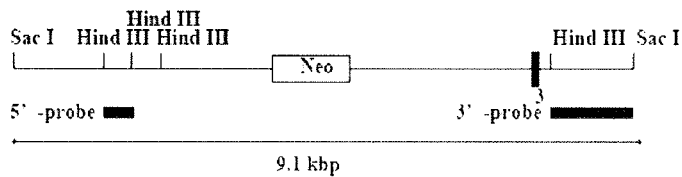
Figure 2:
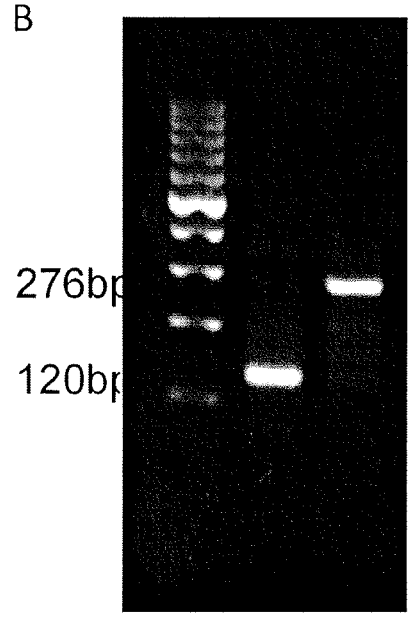
Figure 2:
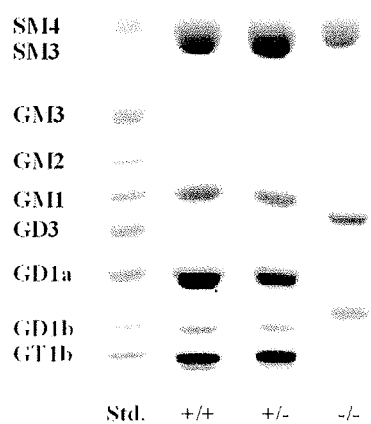

The diagram of a targeting vector used for preparation of the SAT-I KO mouse and confirmation of genetic defect in the KO mouse are shown in FIG. 2A and FIG. 2B, respectively. In FIG. 2A, the targeting vector is shown at the top, and secondly a wild-type gene, and thirdly a variant gene are shown. Further, FIG. 2B shows determination of the SAT-I genotype by PCR. For identification of the wild-type SAT-I allele (exon 2), 5'-GGAATCCATCCCTTTTCTCACAGAG-3 (SEQ ID NO: 5) and 5'-TGAACTCACTTGGCATTGCTGG-3' (SEQ ID NO: 6) were used as primers. For confirmation of SAT-I knockout, the primers of 5'-GGAATCCATCCCTTTTCT-CACAGAG-3' (SEQ ID NO: 7) and 5'-TGAACTCACTTG-GCATTGCTGG-3' (SEQ ID NO: 8) for the neomycin-resistant gene inserted in the genome was used. FIG. 2C shows results of TLC analysis of brain ganglioside. In the wild-type mouse (+/+) and the heterozygous mouse (+/−), GM1, GD1a, GD1b, GT1b, etc. were expressed, while in the knockout mouse (−/−), these all disappeared and GM1b and GD1a were expressed in a compensatory manner (see FIG. 1).

3. Regarding Allergic Response of SAT-I KO Mouse

Figure 3:
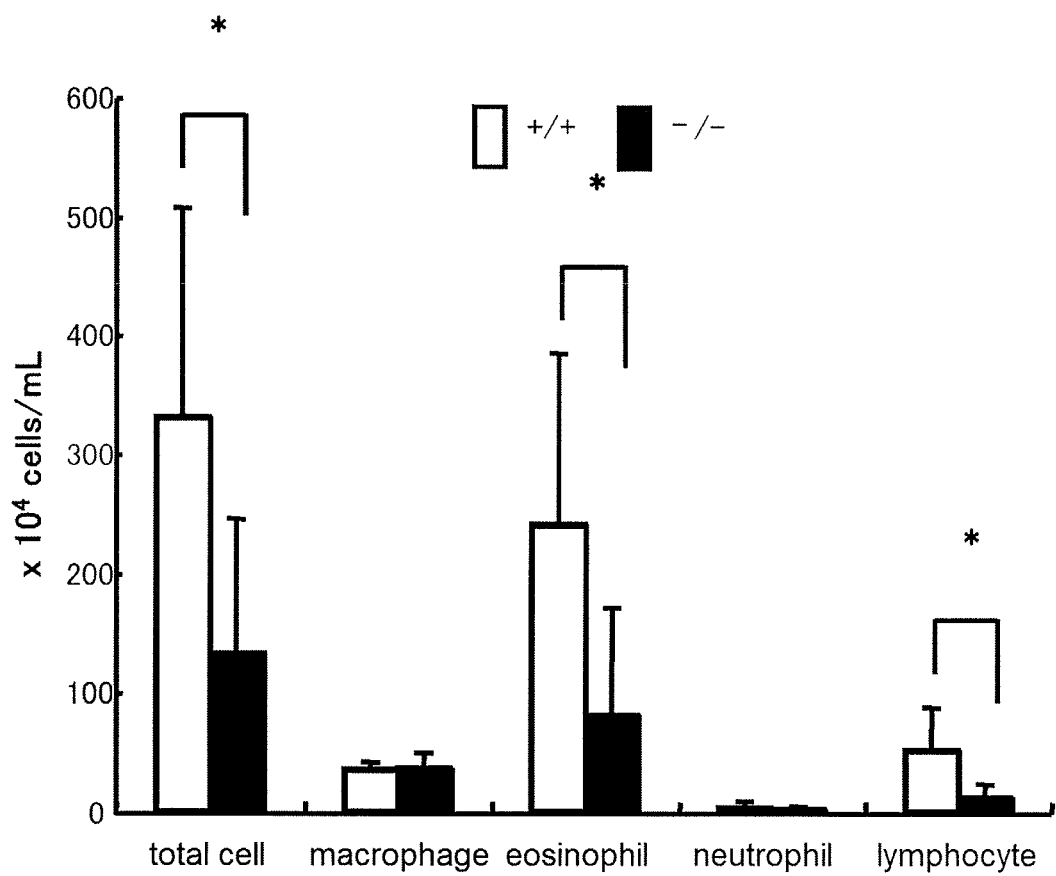
FIG. 3 shows reduction of allergic airway inflammation in a SAT-I gene-deficient mouse after ovalbumin (OVA) inhalation.
Figure 4:
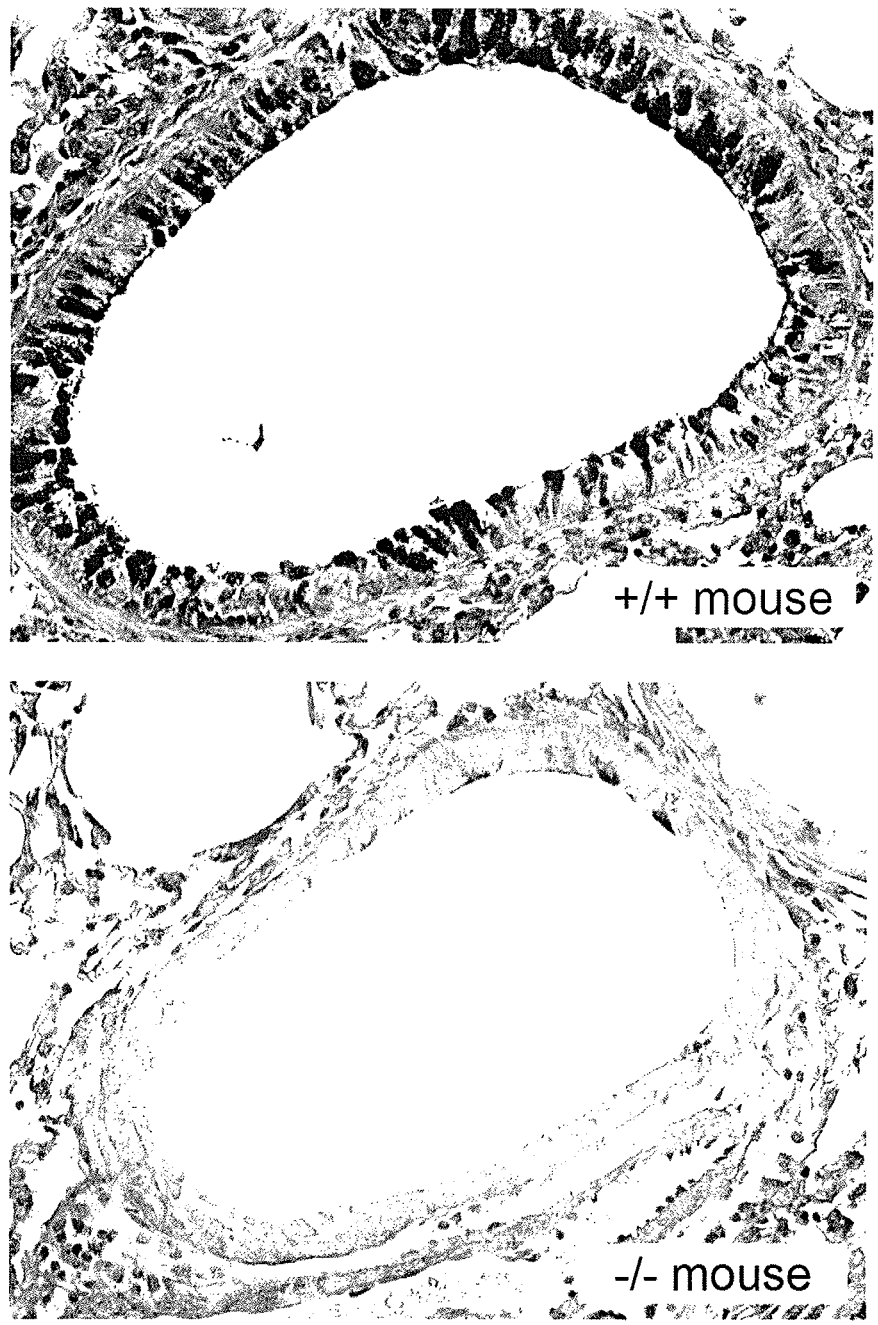
FIG. 4 shows PAS staining of mucosa of the respiratory tract in the SAT-I gene-deficient mouse of FIG. 3 after ovalbumin (OVA) inhalation.

Asthma/allergic reaction of the SAT-I KO mouse caused by ovalbumin (OVA) inhalation after OVA sensitization was examined. The control (wild-type) mouse (+/+) and the SAT-I KO mouse (−/−) were sensitized with OVA by means of intraperitoneal administration and subjected to OVA inhalation 12 days later, thereby inducing asthma/allergic reaction. Asthma/allergic reaction were assessed by collecting lung lavage fluid on day 5 after antigen inhalation and measuring the number of the inflammatory cells therein (FIG. 3). As a result, in the SAT-I KO mouse, the number of the inflammatory cells in the respiratory tract decreased to about 50% or lower compared to that of the control mouse, and in particular, infiltration of lymphocytes and eosinophils decreased to about 30% ($*P<0.05$). Further, on day 5 after antigen inhalation, respiratory tract mucosae of the control (wild-type) mouse (+/+) and the SAT-I KO mouse (−/−) were stained by PAS staining. As a result of staining, the respiratory tract mucosa of the SAT-I KO mouse clearly decreased more compared to that of the control mouse (FIG. 4). Thus, it became clear that the SAT-I KO mouse is resistant to asthma/allergic reaction. Since infiltration of eosinophils to a localized site with allergy is dependent on activation of the helper T cell (see Asthma Prevention and Management Guideline 2006, edited by Japanese Society of Allergology), it is considered that the SAT-I KO mouse lacks the activity of the helper T cell in vivo.

4. Regarding IgE Producing Ability of SAT-I KO Mouse

Figure 5:
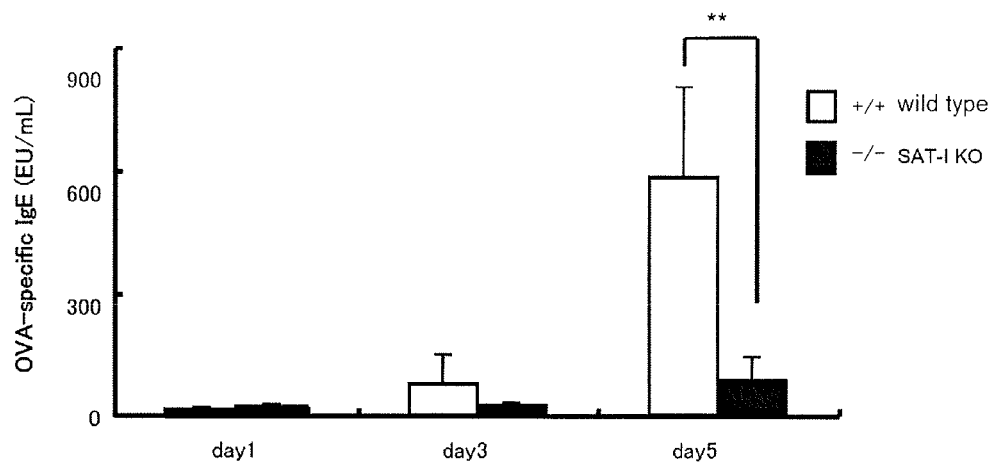
FIG. 5 shows reduction of the amount of IgE in the serum of the SAT-I gene-deficient mouse after ovalbumin (OVA) inhalation.

Therefore, the OVA-specific IgE antibody in serum of the model of asthma/allergy caused by OVA inhalation after OVA sensitization produced according to the above-described method was measured by ELISA. Sera were collected from the same individuals at the time of the assessment of asthma/allergic reaction shown in FIG. 3. As a result, in the SAT-I KO mouse, the amount of the OVA-specific IgE antibody decreased to about 50% or lower compared to that of the control mouse ($**P<0.01$) (FIG. 5). Corresponding to reduction of asthma/allergic reaction in the SAT-I KO mouse (FIG. 3), reduction of the production of the antigen-specific IgE antibody was observed. According to this, it is thought that the function of the IgE class switch in the antibody production was also reduced.

5. Regarding IL-4/IL-5 Producing Ability of SAT-I KO Mouse

Figure 6:
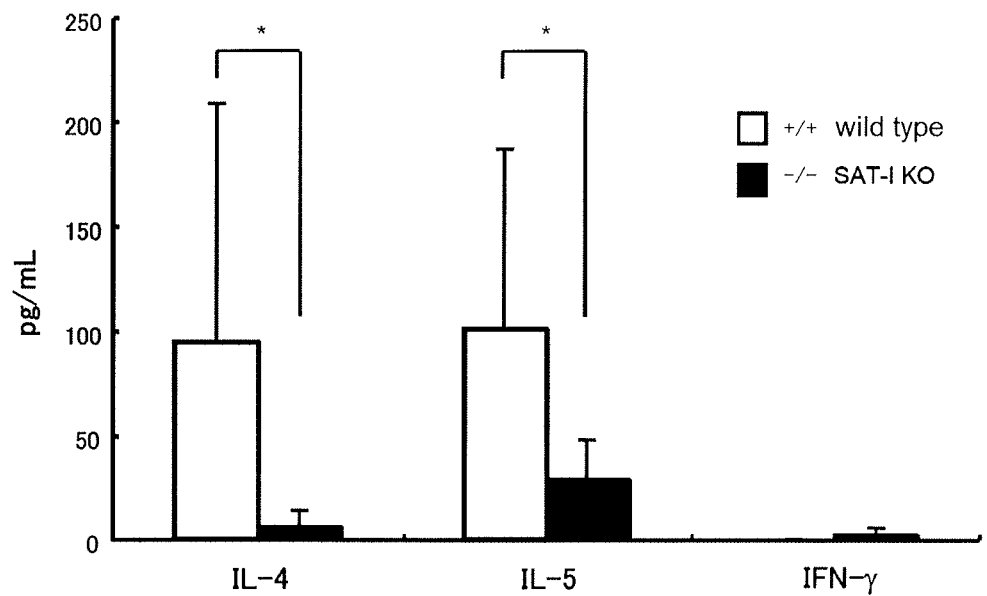
FIG. 6 shows reduction of the serum IL-4 concentration and the serum IL-5 concentration of the SAT-I gene-deficient mouse after ovalbumin (OVA) inhalation.

Since induction of asthma/allergic reaction and production of an antigen-specific IgE antibody are dependent on so-called type II helper T cell cytokines such as IL-4 and IL-5 produced from activated helper T cells (see Allergy Disease Diagnosis and Treatment Guideline 2007, edited by Japanese Society of Allergology), the concentrations of IL-4 and IL-5 in serum of the model with asthma/allergy caused by OVA inhalation after OVA sensitization produced according to the same method as described above were measured by ELISA. Sera were collected from the same individuals at the time of the assessment of asthma/allergic reaction shown in FIG. 3 on day 5 after the antigen inhalation. As a result, in the SAT-I KO mouse, the OVA-specific serum IL-4 concentration and serum IL-5 concentration decreased to about 10% and about 30%, respectively, compared to those of the control mouse ($*P<0.05$) (FIG. 6). Meanwhile, regarding IFN-γ, no significant difference was observed. According to this result, corresponding to reduction of asthma/allergic reaction in the SAT-I KO mouse (FIG. 3), reduction of antigen-specific IL-4 production and IL-5 production was observed.

Figure 7:
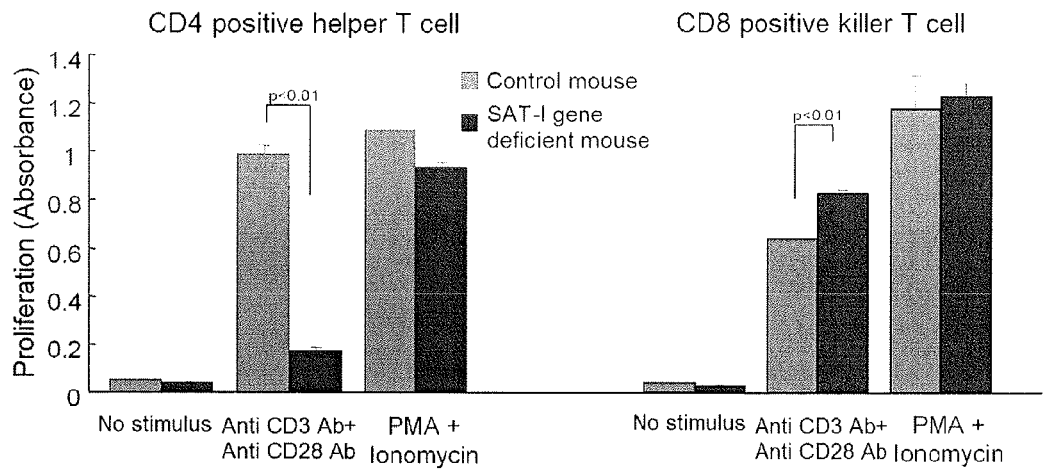
FIG. 7 shows selective suppression of TCR-dependent proliferation response of the CD4 positive T cell in the SAT-I gene-deficient mouse.

6. Regarding T Cell Proliferation of SAT-I KO Mouse 6.1. Regarding TCR-Mediated Proliferation Response of SAT-I KO Mouse-Derived T Cell Next, a series of examinations regarding the mechanisms of the respiratory tract inflammation reaction and reduction of the IgE amount, IL-4 amount and IL-5 amount in serum in the SAT-I KO mouse of the model with asthma/allergic reaction were carried out. T cells of the control and SAT-I KO, in which cell proliferation response upon stimulation with an antibody against a T cell antigen receptor (TCR) was measured, were divided into CD4-positive T cells and CD8-positive T cells, and after that, each of the cells was subjected to no stimulus, stimulus with anti-CD3 antibody+anti-CD28 antibody, or stimulus with PMA+Ionomycin. The cell proliferation at hour 72 was detected using an XTT assay kit (manufactured by R & D systems, MN, USA, catalog number: 4891-025-K). It is publicly known that TCR and the costimulatory molecule CD28 are stimulated with anti-CD3 antibody+anti-CD28 antibody (Immunological Protocol, Hiromitsu Nakauchi Ed., Yodosha Co., Ltd.). Further, regarding PMA, which is phorbol ester and is an activating agent for protein kinase C (for example, available from Sigama-Aldrich Japan, catalog number: P1585), and Ionomycin, which is calcium ionophore and is an agent for increasing the intracellular calcium concentration (e.g., available from Sigama-Aldrich Japan, catalog number: 10634), both of these agents are well known to be forcible activating agents in concurrent usage to force to proliferate cells through providing TCR-bypassed stimulation to the cells (Davis L., and Lipsky P E., Signals involved in T cell activation. II. Distinct roles of intact accessory cells, phorbol esters, and interleukin 1 in activation and cell cycle progression of resting T lymphocytes. J. Immunol. 136, 3558-3596, 1986). As a result, in the CD4-positive T cell of the SAT-I KO mouse, the TCR-dependent proliferation response decreased to about 30% compared to that of the control (the left of FIG. 1). In the case of the stimulus with PMA+Ionomycin, the similar level of the proliferation response as the control was shown. Therefore, it is understood that the SAT-I KO mouse lacks TCR-mediated intracellular signaling. Meanwhile, in the case of the CD8-positive T cell, a tendency that the TCR-mediated proliferation response in the SAT-I KO mouse is stronger was recognized (the right of FIG. 7).

Figure 8:
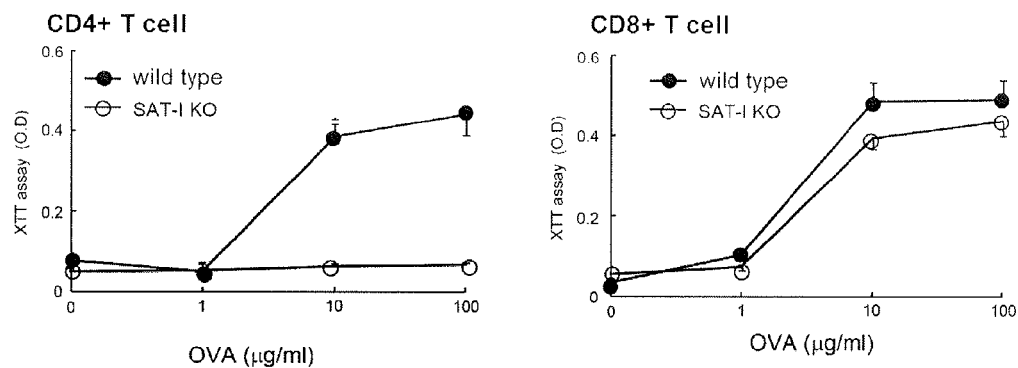
FIG. 8 shows that only the SAT-I KO mouse-derived CD4+ T cell lacks antigen-specific reaction.

6.2. Regarding Antigen-Specific Cell Proliferation of SAT-I KO Mouse-Derived T Cell The wild-type mouse and the SAT-I KO mouse were immunized by subcutaneous injection of trinitrophenol (TNP)-bound OVA (TNP-OVA (200 μg)) as a hapten in the sole. The spleens of the immunized mice were removed at day 8, and CD4+ T cells and CD8+ T cells were respectively purified. These CD4+ T cells and CD8+ T cells were restimulated by an antigen presenting cell+OVA antigen for 72 hours, and antigen-specific T cell proliferation reaction in vitro was then examined (FIG. 8). As a result, it appeared that only the SAT-I KO mouse-derived CD4+ T cell lacks antigen-specific reaction.

Figure 9:
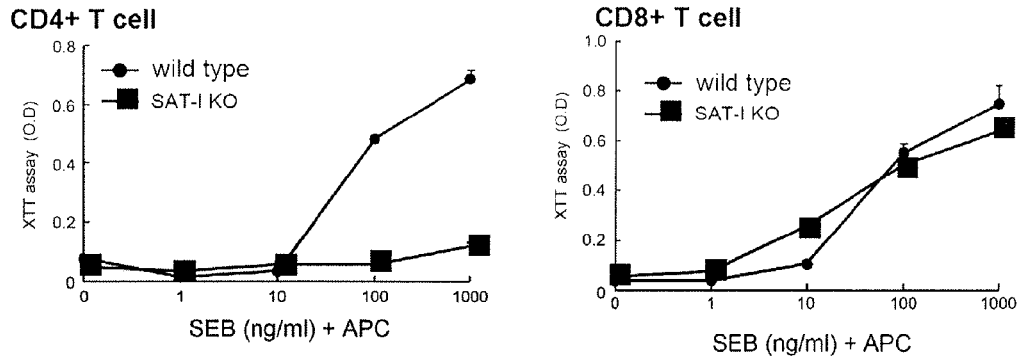
FIG. 9 shows that only the SAT-I KO mouse-derived CD4+ T cell lacks superantigen-specific reaction.

6.3. Regarding Superantigen-Specific Cell Proliferation of SAT-I KO Mouse-Derived T Cell Therefore, it was examined whether or not the selective function reduction of the helper T cell in the SAT-I KO mouse is recognized in the case of a superantigen. As the superantigen, SEB (streptococcul enterotoxin B) which binds to TCR Vb8 was used. This superantigen was added to CD4+ T cells and CD8+ T cells purified from the spleens of the wild-type mouse and the SAT-I KO mouse. Proliferation reaction of the T cells was examined at hour 72 (FIG. 9). As a result, it appeared that only the SAT-I KO mouse-derived CD4+ T cell lacks superantigen-specific reaction.

Figure 10:
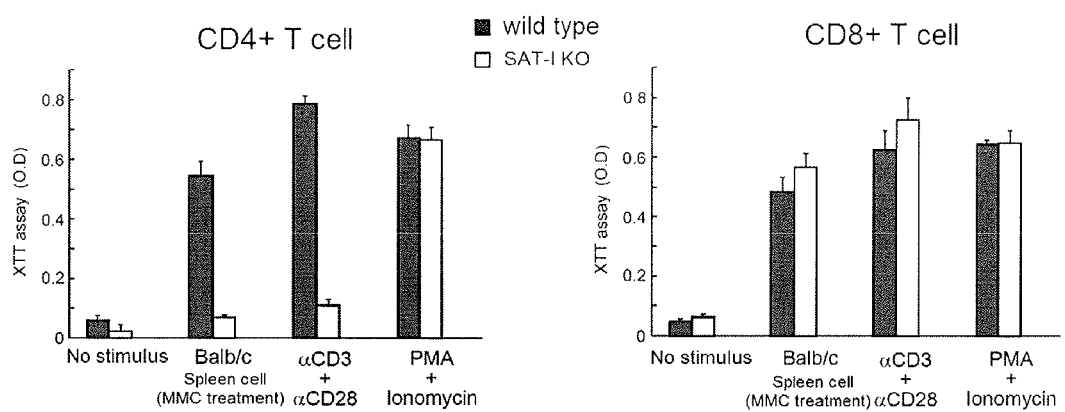
FIG. 10 shows that only the SAT-I KO mouse-derived CD4+ T cell lacks alloantigen-specific reaction.

6.4. Regarding Alloantigen-Specific Cell Proliferation of SAT-I KO Mouse-Derived T Cell Next, in order to examine T cell immune response against an alloantigen (allogeneic antigen), a mixed lymphocyte test (MLR: mixed lymphocyte reaction) was performed (FIG. 10). As responder cells, CD4+ T cells and CD8+ T cells purified from the spleens of the wild-type mouse and the SAT-I KO mouse (both are C57BL/6 line) were used, and stimulator cells were prepared through collecting spleen cells from a Balb/c line mouse and inactivating the cells with mitomycin treatment. The responder cells ($3 \times 10^5$) and the stimulator cells ($6 \times 10^5$) were subjected to mixed culture, and 72 hours later, proliferation reaction and cytokine production were examined. As a result, it appeared that only the SAT-I KO mouse-derived CD4+ T cell lacks alloantigen-specific reaction (FIG. 10).

6.5. Results

Thus, it was demonstrated that in the SAT-I KO mouse, the function of the helper T cell is selectively decreased and on the contrary, the immune function of the killer T cell is normal. That is, it was indicated that gangliosides are elements essential for the immune function of the helper T cell among the T cell subsets.

Accordingly, by controlling expression of SAT-I in the helper T cell or controlling the function of gangliosides, the function of the helper T cell is suppressed to suppress infiltration of eosinophils and lymphocytes, and thereby it is possible to provide resistance to excessive immune response, asthma, allergic reaction, etc. to a subject.

Figure 11:
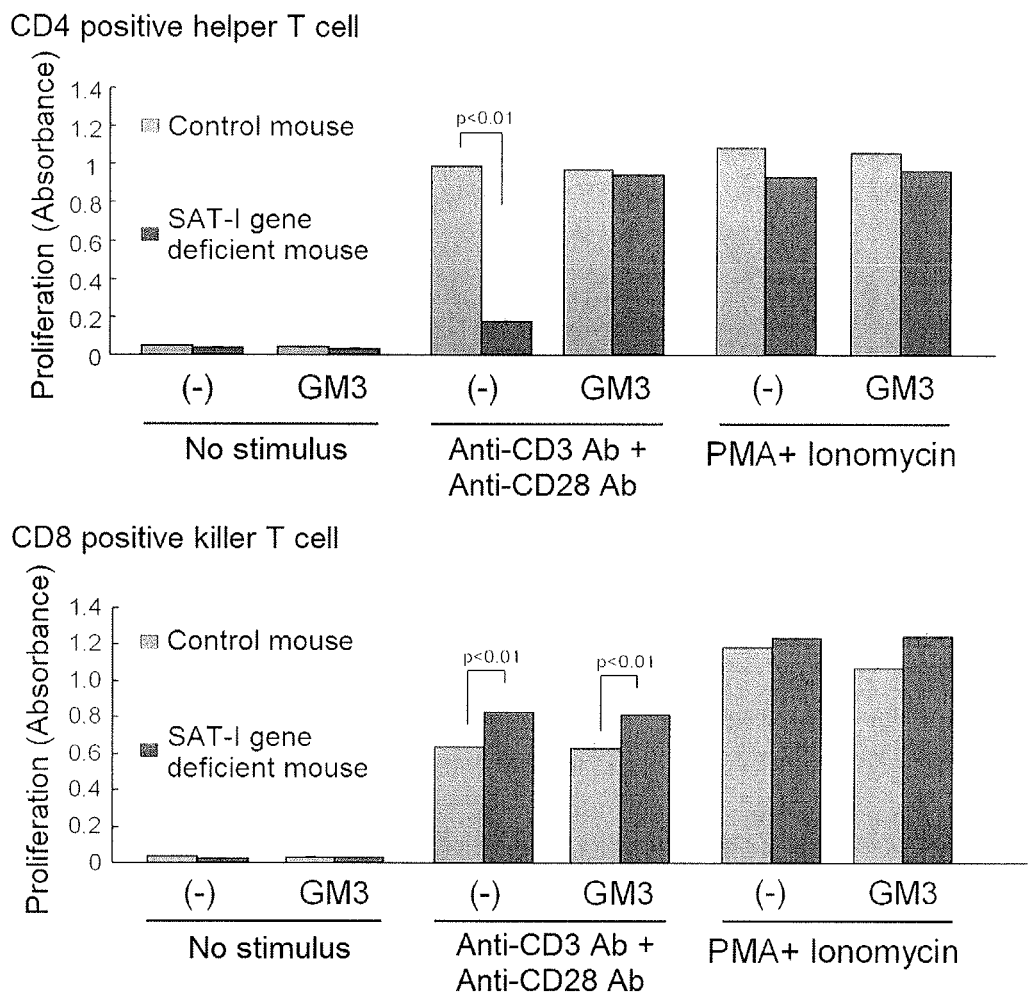
FIG. 11 shows recovering effect of GM3 addition on function reduction of the CD4 positive T cell in the SAT-I gene-deficient mouse.

7. Recovery of T Cell Proliferation Function of SAT-I KO Mouse 7.1. Recovery by GM3 Addition Cell proliferation response upon exogenously supplying ganglioside GM3 to a helper T cell of the SAT-I KO mouse lacking the ganglioside GM3 was measured. T cells of the control mouse and the SAT-I KO mouse were divided into CD4 positive T cells and CD8 positive T cells, and then each of the cells was subjected to no treatment (−) or GM3 treatment (+) for 1 hour. Subsequently, the cells were stimulated by the same method as that of FIG. 1 and cell proliferation was analyzed (FIG. 11). As a result, reduction of TCR-mediated proliferation response in the CD4 positive T cell of the SAT-I KO mouse was completely recovered by GM3 addition.

7.1. Recovery by Reintroduction of SAT-I Gene

Figure 12:
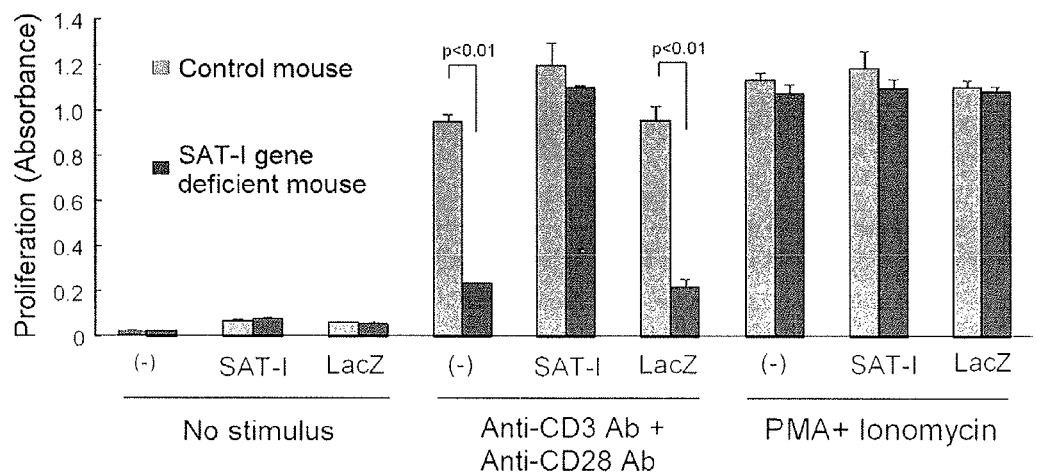
FIG. 12 shows recovering effect of SAT-I gene introduction on function reduction of the CD4 positive T cell in the SAT-I gene-deficient mouse.
Figure 12:
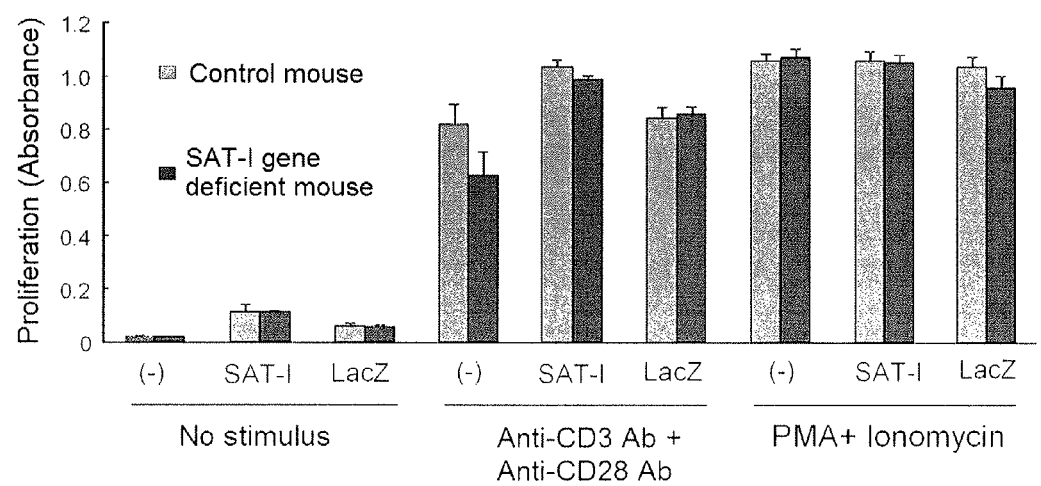

FIG. 12 shows cell proliferation response in the case of reintroducing the SAT-I gene into a helper T cell and a killer T cell from the SAT-I KO mouse. T cells from the control mouse and the SAT-I gene-deficient mouse were divided into CD4 positive T cells and CD8 positive T cells, and then each of the cells was subjected to introduction of the SAT-I gene or the LacZ gene (experiment control) via an adenovirus or no treatment (−). Subsequently, the cells were stimulated with the same method as that of FIG. 1 and cell proliferation was analyzed (Miyake S. et al., Efficient generation of recombinant adenoviruses using adenovirus DNA-terminal protein complex and a cosmid bearing the full-length virus genome. Proc. Natl. Acad. Sci. USA 93, 1320-1324, 1996). As a result, reduction of TCR-mediated proliferation response in the CD4 positive T cell from the SAT-I KO mouse was completely recovered only by reintroduction of the SAT-I gene. Further, no change was recognized in the case where the SAT-I gene was introduced into the CD8 positive T cell.

7.3. Results

According to the above-described results, in the SAT-I KO mouse, selective functional failure of the helper T cell was caused, and antigen-specific cell proliferation of the helper T cell was successfully performed by recovery of the SAT-I activity through gene introduction or supply of GM3 that is a SAT-I product. Therefore, it was confirmed that the helper cell-specific functional failure is caused only by lack of the GM3 synthetic activity of SAT-I.

8. Screening System for Helper T Cell-Specific Immune Response Suppressing Substance

8.1. Purpose

As described above, the SAT-I gene knockout mouse completely lacks the gangliosides of a-series, b-series and c-series (FIG. 1). As a result, TCR-mediated proliferation response was reduced in a helper T cell-specific manner, and reduction of various immune responses was recognized. Currently, no helper T cell-specific immunosuppressive substance has been reported with attention focused on the SAT-I synthetase or GM3 synthesis pathway. Therefore, by utilizing the experimental system in which the SAT-I activity is lacked or reduced as described herein, the below-described screening method, in which a pharmacological substance can be identified that is effective for excessive immune response, asthma, allergic reaction, etc., was developed.

8.2. Main Materials and Principles

Regarding the sphingoglycolipid biosynthesis inhibitors, D-PDMP (D-threo-1-phenyl-2-decanoylamiono-3-morpholino-1-prppanol.HCl, product name: D-threo-PDMP; manufacturer: Matreya, Inc.; catalog number: #1756), D-PPMP (D-threo-1-phenyl-2-hexadecanoylamiono-3-morpholino-1-prppanol.HCl; manufacturer: Matreya, Inc.; catalog number: #1865), D-PBPP (D-threo-1-phenyl-2-benzyloxycarbonylamino-3-pyrrolidinoamino-1-prppanol.HCl: Jimbo et al., J. Biochem. 127 485-491, 2000), D-threo-3',4'-Ethylenedioxy-P4 (D-threo-3',4'-Ethylenedioxy 1-phenyl-2-palmitoylamino-3-pyrrolidino-1-propanol, title of document: Lee, L., et al., J Biol Chem. 274, 14662-14669, 1999) and analogous compounds thereof, and AMP-DNM (N-(5-adamantane-1-yl-methoxy)-pentyl-1-deoxynojirimycin, Diabetes 56, 1341-1349, 2007) which has a different basic structure, these inhibit glucosylceramide (GlcCer) synthetase selectively in sphingoglycolipid biosynthesis, and suppress production of all of the gangliosides (see the upper left portion of FIG. 1). Therefore, when treated with a GlcCer synthetase inhibitor such as D-PDMP, both the function of the CD4 positive T cell and the function of the CD8 positive T cell are suppressed (Nagafuku, M., et al., J. Biol. Chem. 278, 51920-51927, 2003. ; Blank N. et al., Biochem. Pharmacol. 126-135, 2005). Therefore, in order to clarify that it is possible to screen a substance for selectively suppressing the function of the CD4 positive T cell, all T cells are treated with a GlcCer synthetase inhibitor, and after the treatment or simultaneously with the treatment, GM3 is added to a culture solution to confirm recovery of the function (proliferation ability) of the CD4 positive T cell. At this time, the GlcCer synthetase inhibitor also suppresses the function of the CD8 positive T cell, while, in spite of GM3 addition, the proliferation ability of the CD8 positive T cell is not recovered.

Reference Example 1

Development of Screening System 1 (In Vitro System)
Experimental Procedure

CD4 positive T cells are purified from lymph node cells of a wild-type mouse, and $2 \times 10^5$ cells are seeded in a 96-well plate and subjected to no stimulus, stimulus with anti-CD3 antibody+anti-CD28 antibody, or stimulus with PMA+Ionomycin. Simultaneously with the stimulus, both, either or none of a glucosylceramide (GlcCer) synthetase inhibitor (e.g., D-PDMP (10 μM)) and GM3 (2 μg/ml) are/is added. About 72 hours later, cell proliferation response is assessed with XTT assay. In this experimental system, when glycolipids are exhausted, cell proliferation associated with activation of CD4 T cells is suppressed, while in coexistence of GM3 the proliferation suppression effect of D-PDMP is canceled. Therefore, a method for screening an effective compound for suppressing the activity of the helper T cell can be established.

Reference Example 2

Development of Screening System 2 (In Vivo System)
Experimental Procedure

A control (wild-type) mouse (+/+) and a SAT-I KO mouse (−/−) are sensitized with OVA twice by means of intraperitoneal administration and subjected to OVA inhalation several days later, thereby inducing asthma/allergic reaction. A glucosylceramide synthetase inhibitor (e.g., D-PDMP) is dissolved in 5% Tween 80 at a concentration of 10 mg/ml or the like, and under such a condition that the CD4 positive T cell is proliferated only in the case of using GM3 in combination, for example, 75 mg/kg of the mixture is intraperitoneally administered twice a day for 6 consecutive days starting before OVA inhalation. Assessment of asthma/allergic reaction can be carried out using the above-described various methods, such as measurement of the number of inflammatory cells contained in a lung lavage fluid and the amount of cytokine, staining of respiratory tract mucus (the main component of expectorated sputum) of lung tissue, and measuring the amount of anti-OVA-specific IgE in serum, as in the case of using the SAT-I KO mouse.

INDUSTRIAL APPLICABILITY

The present invention is an innovative and epoch-making invention which enables selective function control of a helper T cell. It is expected that a novel treatment method targeting infectious disease, tumor, rejection caused by transplantation of organs, allergy, etc. will be developed based on the invention.

The invention claimed is:

1. A screening method, wherein the method comprises:
   contacting a test substance with a helper T cell;
   measuring the production amount of GM3 in the helper T cell;
   selecting the test substance that reduces the amount of GM3 as compared to a control by specifically reducing the GM3 synthase expression in the helper T cell;
   administering the selected test substance to a non-human animal having an immune disease, asthma, and/or indicating an allergic reaction; and
   selecting the administered test substance that has an immunosuppressive action, an anti-asthmatic action, and/or an anti-allergic action as compared to a control animal.

2. The method according to claim 1, wherein the non-human animal is a mouse.

3. The method according to claim 1, wherein the method further comprises comparing the number of infiltrating cells of macrophages, neutrophils, eosinophils, and/or lymphocytes in an inflammatory site of the non-human animal with that of a control animal.

* * * * *